United States Patent
Cabiri et al.

(10) Patent No.: US 9,421,323 B2
(45) Date of Patent: Aug. 23, 2016

(54) DOOR AND DOORSTOP FOR PORTABLE ONE USE DRUG DELIVERY APPARATUS

(71) Applicant: MEDIMOP Medical Projects Ltd., Ra'anana (IL)

(72) Inventors: Oz Cabiri, Macabim-Reut (IL); Reuven Y. Filman, Netanya (IL); Tomer Solomon, Modiin (IL)

(73) Assignee: MEDIMOP MEDICAL PROJECTS LTD., Ra'anana (IL)

( * ) Notice: Subject to any disclaimer, the term of this patent is extended or adjusted under 35 U.S.C. 154(b) by 670 days.

(21) Appl. No.: 13/733,516

(22) Filed: Jan. 3, 2013

(65) Prior Publication Data

US 2014/0188073 A1 Jul. 3, 2014

(51) Int. Cl.
  *A61M 5/31* (2006.01)
  *A61M 5/142* (2006.01)
  *A61M 5/24* (2006.01)
  *A61M 5/145* (2006.01)

(52) U.S. Cl.
  CPC ........... *A61M 5/14244* (2013.01); *A61M 5/24* (2013.01); *A61M 2005/14573* (2013.01); *A61M 2005/2407* (2013.01); *A61M 2205/276* (2013.01)

(58) Field of Classification Search
  CPC ............... A61M 5/14248; A61M 2005/2407; A61M 2005/2496; A61M 5/24; A61M 2005/14573; A61M 2005/2414; A61M 2005/1468; A61M 5/14566; A61M 2005/2411; A61M 2005/2488; A61M 2005/2492; A61M 2205/276; A61M 5/14244; A61M 5/1456
  See application file for complete search history.

(56) References Cited

U.S. PATENT DOCUMENTS

| 1,795,630 A | 3/1931 | Wilson |
| 2,860,635 A | 11/1958 | Wilburn |
| 3,203,269 A | 8/1965 | Perrine |
| 3,212,685 A | 10/1965 | Swan et al. |
| 3,794,028 A | 2/1974 | Mueller et al. |
| 3,994,295 A | 11/1976 | Wulff |

(Continued)

FOREIGN PATENT DOCUMENTS

| CN | 1747683 A | 3/2006 |
| CN | 1863566 A | 11/2006 |

(Continued)

OTHER PUBLICATIONS

Office Action issued Jun. 3, 2014 in JP Application No. 2010-527595.

(Continued)

*Primary Examiner* — Kevin C Sirmons
*Assistant Examiner* — William Carpenter
(74) *Attorney, Agent, or Firm* — Panitch Schwarze Belisario & Nadel LLP

(57) ABSTRACT

An aspect of some embodiments of the current application is a doorstop to a drug delivery apparatus that encourages a user of the apparatus to perform the proper usage steps in the proper order. For example, a user may be expected to receive an injector in a transport state, open it to an open state, insert a cartridge, and/or close the cartridge before operation. The doorstop may have an obstructing mode, optionally preventing closing of the door. The cartridge may optionally have a non-obstructing mode allowing closing of the door. Inserting the cartridge may optionally cause a doorstop to move from the obstructing mode to the non-obstructing mode. In the non-obstructing mode the doorstop may optionally prevent removal of the cartridge.

15 Claims, 18 Drawing Sheets

(56) References Cited

U.S. PATENT DOCUMENTS

| | | |
|---|---|---|
| 4,195,636 A | 4/1980 | Behnke |
| 4,218,724 A | 8/1980 | Kaufman |
| 4,273,122 A | 6/1981 | Whitney et al. |
| 4,300,554 A | 11/1981 | Hessberg et al. |
| 4,403,987 A | 9/1983 | Gottinger |
| 4,435,173 A | 3/1984 | Siposs et al. |
| 4,465,478 A | 8/1984 | Sabelman et al. |
| 4,565,543 A | 1/1986 | Bekkering et al. |
| 4,585,439 A | 4/1986 | Michel |
| 4,599,082 A | 7/1986 | Grimard |
| 4,601,702 A | 7/1986 | Hudson |
| 4,685,903 A | 8/1987 | Cable et al. |
| 4,689,043 A * | 8/1987 | Bisha ............ A61M 5/142 128/DIG. 13 |
| 4,698,055 A | 10/1987 | Sealfon |
| 4,810,215 A | 3/1989 | Kaneko |
| 4,850,966 A | 7/1989 | Grau et al. |
| 4,867,743 A | 9/1989 | Vaillancourt |
| 4,886,499 A | 12/1989 | Cirelli et al. |
| 4,919,596 A | 4/1990 | Slate et al. |
| 4,929,241 A | 5/1990 | Kulli |
| 4,950,246 A | 8/1990 | Muller |
| D322,671 S | 12/1991 | Szwarc |
| 5,090,877 A * | 2/1992 | D'Silva ............ E05B 17/0058 417/474 |
| 5,109,850 A | 5/1992 | Blanco et al. |
| 5,112,317 A | 5/1992 | Michel |
| 5,131,816 A | 7/1992 | Brown et al. |
| 5,190,521 A | 3/1993 | Hubbard et al. |
| 5,254,096 A | 10/1993 | Rondelet et al. |
| 5,300,045 A | 4/1994 | Plassche, Jr. |
| 5,342,313 A | 8/1994 | Campbell et al. |
| 5,348,544 A | 9/1994 | Sweeney et al. |
| 5,364,364 A * | 11/1994 | Kasvikis ............ A61M 5/14228 137/556 |
| 5,366,498 A | 11/1994 | Brannan et al. |
| 5,383,865 A | 1/1995 | Michel |
| 5,445,621 A * | 8/1995 | Poli ............ A61M 5/1413 604/246 |
| 5,478,315 A | 12/1995 | Brothers et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A * | 4/1996 | Funderburk ........ A61M 5/1456 604/151 |
| 5,562,686 A | 10/1996 | Sauer et al. |
| 5,593,390 A | 1/1997 | Castellano et al. |
| 5,616,132 A | 4/1997 | Newman |
| 5,643,218 A | 7/1997 | Lynn et al. |
| 5,645,955 A | 7/1997 | Maglica |
| 5,647,853 A | 7/1997 | Feldmann et al. |
| 5,662,678 A | 9/1997 | Macklin |
| 5,672,160 A | 9/1997 | Osterlind et al. |
| 5,690,618 A | 11/1997 | Smith et al. |
| D393,314 S | 4/1998 | Meisner et al. |
| 5,766,186 A | 6/1998 | Faraz et al. |
| 5,779,676 A * | 7/1998 | Kriesel ............ A61M 5/152 604/132 |
| 5,795,675 A | 8/1998 | Maglica |
| 5,800,420 A | 9/1998 | Gross et al. |
| 5,807,375 A | 9/1998 | Gross et al. |
| 5,814,020 A | 9/1998 | Gross |
| 5,830,187 A * | 11/1998 | Kriesel ............ A61M 5/152 604/132 |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,931,814 A | 8/1999 | Alex et al. |
| 5,941,850 A | 8/1999 | Shah et al. |
| 5,948,392 A | 9/1999 | Haslwanter et al. |
| 5,954,697 A * | 9/1999 | Srisathapat ........ A61M 5/1456 604/154 |
| 5,957,895 A | 9/1999 | Sage et al. |
| 5,968,011 A | 10/1999 | Larsen et al. |
| 5,993,423 A | 11/1999 | Choi |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,064,797 A | 5/2000 | Crittendon et al. |
| 6,074,369 A | 6/2000 | Sage et al. |
| 6,186,982 B1 | 2/2001 | Gross et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,377,848 B1 | 4/2002 | Garde et al. |
| 6,391,005 B1 | 5/2002 | Lum et al. |
| 6,423,029 B1 | 7/2002 | Elsberry |
| 6,423,036 B1 * | 7/2002 | Van Huizen ...... A61M 17/3417 604/117 |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,558,351 B1 | 5/2003 | Steil et al. |
| 6,589,229 B1 | 7/2003 | Connelly et al. |
| 6,595,956 B1 | 7/2003 | Gross et al. |
| 6,595,960 B2 | 7/2003 | West et al. |
| 6,599,272 B1 * | 7/2003 | Hjertman ............ A61M 5/315 604/197 |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,689,118 B2 | 2/2004 | Alchas et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,787 B1 | 6/2004 | Causey, III et al. |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,960,192 B1 | 11/2005 | Flaherty et al. |
| 6,997,727 B1 | 2/2006 | Legrady et al. |
| 7,001,360 B2 | 2/2006 | Veasey et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,097,637 B2 | 8/2006 | Triplett et al. |
| 7,128,727 B2 | 10/2006 | Flaherty et al. |
| 7,144,384 B2 | 12/2006 | Gorman et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |

(56) References Cited

U.S. PATENT DOCUMENTS

| | | |
|---|---|---|
| 7,291,132 B2 | 11/2007 | DeRuntz et al. |
| 7,291,159 B2 | 11/2007 | Schmelzeisen-Redeker et al. |
| 7,303,549 B2 | 12/2007 | Flaherty et al. |
| 7,344,385 B2 | 3/2008 | Chen |
| 7,364,570 B2 | 4/2008 | Gerondale et al. |
| 7,390,314 B2 | 6/2008 | Stutz, Jr. et al. |
| 7,407,493 B2 | 8/2008 | Cane' |
| D578,210 S | 10/2008 | Muta et al. |
| 7,455,663 B2 | 11/2008 | Bikovsky |
| 7,465,290 B2 | 12/2008 | Reilly |
| 7,488,181 B2 | 2/2009 | van Haaster |
| 7,497,842 B2 | 3/2009 | Diaz et al. |
| 7,501,587 B2 | 3/2009 | English |
| 7,503,786 B2 | 3/2009 | Kato et al. |
| 7,530,964 B2 | 5/2009 | Lavi et al. |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,801,599 B2 | 9/2010 | Young et al. |
| 7,806,868 B2 | 10/2010 | De Polo et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | McGrath et al. |
| 8,308,679 B2 | 11/2012 | Hanson et al. |
| 8,323,250 B2 | 12/2012 | Chong et al. |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,628,510 B2 | 1/2014 | Bazargan et al. |
| 8,674,288 B2 | 3/2014 | Hanson et al. |
| 8,679,060 B2 | 3/2014 | Mernoe et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |

(56) References Cited

U.S. PATENT DOCUMENTS

| | | |
|---|---|---|
| 8,814,379 B2 | 8/2014 | Griffiths et al. |
| 8,920,374 B2 | 12/2014 | Bokelman et al. |
| 9,061,104 B2 | 6/2015 | Daniel |
| 9,061,110 B2 | 6/2015 | Avery et al. |
| 9,089,475 B2 | 7/2015 | Fangrow |
| 9,089,641 B2 | 7/2015 | Kavazov |
| 2001/0025168 A1 | 9/2001 | Gross et al. |
| 2001/0041869 A1 | 11/2001 | Causey et al. |
| 2002/0010423 A1 | 1/2002 | Gross et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0065488 A1 | 5/2002 | Suzuki et al. |
| 2002/0107487 A1 | 8/2002 | Preuthun |
| 2002/0123740 A1 | 9/2002 | Flaherty et al. |
| 2002/0161332 A1 | 10/2002 | Ramey |
| 2002/0169215 A1 | 11/2002 | Meng |
| 2003/0009133 A1 | 1/2003 | Ramey |
| 2003/0109827 A1 | 6/2003 | Lavi et al. |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2004/0010207 A1 | 1/2004 | Flaherty et al. |
| 2004/0015131 A1 | 1/2004 | Flaherty et al. |
| 2004/0064088 A1 | 4/2004 | Gorman et al. |
| 2004/0092873 A1 | 5/2004 | Moberg |
| 2004/0116866 A1 | 6/2004 | Gorman et al. |
| 2004/0127857 A1 | 7/2004 | Shemesh et al. |
| 2004/0158172 A1 | 8/2004 | Hancock |
| 2004/0186419 A1 | 9/2004 | Cho |
| 2004/0260233 A1 | 12/2004 | Garibotto et al. |
| 2005/0033234 A1 | 2/2005 | Sadowski et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | DiIanni et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0095014 A1 | 5/2006 | Ethelfeld |
| 2006/0122577 A1 | 6/2006 | Poulsen et al. |
| 2006/0173406 A1 | 8/2006 | Hayes et al. |
| 2006/0173439 A1 | 8/2006 | Thorne et al. |
| 2006/0195029 A1 | 8/2006 | Shults et al. |
| 2006/0211982 A1 | 9/2006 | Prestrelski et al. |
| 2006/0229569 A1 | 10/2006 | Lavi et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0049865 A1 | 3/2007 | Radmer et al. |
| 2007/0073228 A1 | 3/2007 | Mernoe et al. |
| 2007/0118405 A1 | 5/2007 | Campbell et al. |
| 2007/0167912 A1 | 7/2007 | Causey et al. |
| 2007/0185449 A1 | 8/2007 | Mernoe |
| 2007/0197968 A1* | 8/2007 | Pongpairochana ..... A61M 5/20 604/131 |
| 2007/0203454 A1 | 8/2007 | Shermer et al. |
| 2007/0233038 A1 | 10/2007 | Pruitt et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097381 A1 | 4/2008 | Moberg et al. |
| 2008/0108951 A1 | 5/2008 | Jerde et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0208138 A1 | 8/2008 | Lim et al. |
| 2008/0215006 A1 | 9/2008 | Thorkild |
| 2008/0215015 A1 | 9/2008 | Cindrich et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0041805 A1 | 2/2009 | Walker |
| 2009/0048347 A1 | 2/2009 | Cohen et al. |
| 2009/0054750 A1 | 2/2009 | Jennewine |
| 2009/0069784 A1 | 3/2009 | Estes et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0124977 A1 | 5/2009 | Jensen |
| 2009/0143730 A1 | 6/2009 | De Polo et al. |
| 2009/0143735 A1 | 6/2009 | De Polo et al. |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0049128 A1 | 2/2010 | McKenzie et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0081993 A1 | 4/2010 | O'Connor |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0211011 A1 | 8/2010 | Haar |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0280499 A1 | 11/2010 | Yodfat et al. |
| 2010/0331826 A1 | 12/2010 | Field et al. |

(56) References Cited

U.S. PATENT DOCUMENTS

| | | |
|---|---|---|
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0066131 A1* | 3/2011 | Cabiri ............... A61M 5/14248 604/411 |
| 2011/0125056 A1 | 5/2011 | Merchant |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178472 A1 | 7/2011 | Cabiri |
| 2011/0201998 A1 | 8/2011 | Pongpairochana et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0226234 A1 | 9/2012 | Bazargan et al. |
| 2012/0259282 A1 | 10/2012 | Alderete, Jr. et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0253419 A1 | 9/2013 | Favreau |
| 2013/0253420 A1 | 9/2013 | Favreau |
| 2013/0253421 A1 | 9/2013 | Favreau |
| 2013/0296799 A1 | 11/2013 | Degtiar et al. |
| 2013/0304021 A1 | 11/2013 | Cabiri et al. |
| 2013/0323699 A1 | 12/2013 | Edwards et al. |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |

FOREIGN PATENT DOCUMENTS

| | | |
|---|---|---|
| CN | 101090749 A | 12/2007 |
| CN | 201941304 U | 8/2011 |
| CN | 102186733 A | 9/2011 |
| DE | 1064693 B | 9/1959 |
| EP | 0017412 A1 | 10/1980 |
| EP | 0222656 A1 | 5/1987 |
| EP | 0401179 A1 | 12/1990 |
| EP | 1530979 A1 | 5/2005 |
| EP | 1666080 A1 | 6/2006 |
| EP | 2060606 A1 | 5/2009 |
| EP | 2498589 A1 | 9/2012 |
| JP | H07-194701 A | 8/1995 |
| JP | H09-505758 A | 6/1997 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-527138 A | 9/2003 |
| JP | 2003-534061 A | 11/2003 |
| JP | 2004-501721 A | 1/2004 |
| JP | 2004-512100 A | 4/2004 |
| JP | 2005-523127 A | 8/2005 |
| JP | 2005-270629 A | 10/2005 |
| JP | 2007-509661 A | 4/2007 |
| JP | 2008-534131 A | 8/2008 |
| JP | 2008-220961 A | 9/2008 |
| JP | 2009-502273 A | 1/2009 |
| WO | 9009202 A1 | 8/1990 |
| WO | 9307922 A1 | 4/1993 |
| WO | 9407553 A1 | 4/1994 |
| WO | 9513838 A1 | 5/1995 |
| WO | 9609083 A1 | 3/1996 |
| WO | 9632975 A1 | 10/1996 |
| WO | 9700091 A1 | 1/1997 |
| WO | 9710012 A1 | 3/1997 |
| WO | 9733638 A1 | 9/1997 |
| WO | 9857683 A1 | 12/1998 |
| WO | 9929151 A1 | 6/1999 |
| WO | 9959665 A1 | 11/1999 |
| WO | 0025844 A1 | 5/2000 |
| WO | 0187384 A1 | 11/2001 |
| WO | 0189607 A2 | 11/2001 |
| WO | 0189613 A1 | 11/2001 |
| WO | 0202165 A2 | 1/2002 |
| WO | 0234315 A1 | 5/2002 |
| WO | 0272182 A1 | 9/2002 |
| WO | 03090833 A1 | 11/2003 |
| WO | 2004032990 A2 | 4/2004 |
| WO | 2004105841 A1 | 12/2004 |
| WO | 2005018703 A2 | 3/2005 |
| WO | 2005037350 A2 | 4/2005 |
| WO | 2006037434 A1 | 4/2006 |
| WO | 2006069380 A1 | 6/2006 |
| WO | 2006102676 A1 | 9/2006 |
| WO | 2006104806 A2 | 10/2006 |
| WO | 2007051563 A1 | 5/2007 |
| WO | 2007056504 A1 | 5/2007 |
| WO | 2008001377 A2 | 1/2008 |
| WO | 2008014908 A1 | 2/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2009044401 | 4/2009 |
| WO | 2009046989 A2 | 4/2009 |
| WO | 2009125398 A2 | 10/2009 |
| WO | 2009144085 A2 | 12/2009 |
| WO | 2010078227 A1 | 7/2010 |
| WO | 2010078242 A1 | 7/2010 |
| WO | 2011075105 A1 | 6/2011 |
| WO | 2011090955 A1 | 7/2011 |

(56) References Cited

FOREIGN PATENT DOCUMENTS

| WO | 2011090956 A2 | 7/2011 | | |
|---|---|---|---|---|
| WO | 2011156373 A1 | 12/2011 | | |
| WO | 2012032411 A2 | 3/2012 | | |
| WO | 2012040528 A1 | 3/2012 | | |
| WO | WO 2012032411 A2 * | 3/2012 | ........ | A61M 5/14244 |
| WO | 2012160157 A1 | 11/2012 | | |
| WO | 2014179774 A1 | 11/2014 | | |

OTHER PUBLICATIONS

Office Action issued Jul. 7, 2014 in U.S. Appl. No. 12/244,666 by Gross.
Int'l Search Report and Written Opinion issued Jul. 31, 2014 in Int'l Application No. PCT/US2014/033598.
Daikyo Crystal Zenith® polymer, Manufactured by Daikyo Seiko, Ltd.
Copaxone®, Manufactured by Teva Pharmaceutical Industries Ltd.
Int'l Search Report issued May 13, 2009 in Int'l Application No. PCT/IL2008/001312.
Int'l Preliminary Report on Patentability issued Apr. 7, 2010 in Int'l Application No. PCT/IL2008/001312: Written Opinion.
Int'l Search Report issued Apr. 26, 2010 in Int'l Application No. PCT/US2009/069552.
Office Action issued Apr. 5, 2010 in U.S. Appl. No. 12/244,666.
Office Action issued Sep. 21, 2010 in U.S. Appl. No. 12/244,666.
Office Action issued Apr. 5, 2010 in U.S. Appl. No. 12/244,688.
Office Action issued Sep. 2, 2010 in U.S. Appl. No. 12/244,688.
Office Action issued Sep. 30, 2010 in U.S. Appl. No. 12/689,250.
Int'l Search Report issued Jan. 12, 2011 in Int'l Application No. PCT/US2010/048556; Written Opinion.
International Preliminary Report on Patentability issued on Jul. 5, 2011 in International Application No. PCT/US2009/069552; Written Opinion.
Office Action issued Jul. 13, 2011 in U.S. Appl. No. 12/559,563.
Int'l Preliminary Report on Patentability issued Sep. 1, 2011 in Int'l Application No. PCT/US2010/048556.
Office Action issued Sep. 6, 2011 in U.S. Appl. No. 12/345,818.
Office Action issued Feb. 21, 2012 in U.S. Appl. No. 12/689,249.
Int'l Search Report issued Jun. 17, 2011 in Int'l Application No. PCT/US2011/021604.
Int'l Search Report issued Oct. 12, 2011 in Int'l Application No. PCT/US2011/021605.
Office Action issued Oct. 28, 2011 in U.S. Appl. No. 12/615,828.
Int'l Search Report issued Sep. 22, 2011 in Int'l Application No. PCT/IL11/00368; Written Opinion.
U.S. Appl. No. 13/521,181 by Cabiri, filed Jul. 9, 2012.
U.S. Appl. No. 13/521,167 by Cabiri, filed Jul. 9, 2012.
Office Action issued May 16, 2012 in U.S. Appl. No. 12/615,828.
Office Action issued Jul. 2, 2012 in U.S. Appl. No. 13/272,555.
Office Action issued May 3, 2012 in CN Application No. 200880117084.X.
U.S. Appl. No. 13/472,112 by Cabiri, filed May 15, 2012.
U.S. Appl. No. 13/429,840 by Cabiri, filed Mar. 26, 2012.
Int'l Preliminary Report on Patentability issued Aug. 2, 2012 in Int'l Application No. PCT/US2011/021604.
U.S. Appl. No. 13/643,470 by Alon, filed Oct. 25, 2012.
Office Action issued Dec. 17, 2013 in JP Application No. 2012-529808.
Office Action issued Dec. 10, 2013 in CN Application No. 201180006567.4.
Office Action issued Jan. 8, 2014 in U.S. Appl. No. 13/521,167 by Cabiri.
U.S. Appl. No. 29/479,307 by Norton, filed Jan. 14, 2014.
U.S. Appl. No. 14/593,051 by Gross, filed Jan. 9, 2015.
Office Action issued Jan. 8, 2013 in JP Application No. 2010-527595.
Int'l Preliminary Report on Patentability issued Feb. 7, 2013 in Int'l Application No. PCT/US2011/021604.
Int'l Preliminary Report on Patentability issued Feb. 7, 2013 in Int'l Application No. PCT/US2011/021605.
English translation of an Office Action issued Jan. 30, 2013 in CN Application No. 200880117084.X.
U.S. Appl. No. 14/193,692 by Gross, filed Feb. 28, 2014.
Office Action issued Feb. 4, 2014 in EP Application No. 11 707 942.6.
English translation of an Office Action issued Mar. 5, 2014 in CN Application No. 200880117084.X.
Int'l Search Report and Written Opinion issued Apr. 3, 2014 in Int'l Application No. PCT/US2013/078040.
Extended European Search Report issued Mar. 27, 2014 in EP Application No. 14154717.4.
Office Action issued Feb. 28, 2014 in CN Application No. 201180006571.0.
Int'l Preliminary Report on Patentability issued May 14, 2015 in Int'l Application No. PCT/US2013/065211.
Office Action issued May 7, 2015 in JP Application No. 2012-550069.
Office Action issued May 13, 2015 in CN Application No. 201380025566.3.
U.S. Appl. No. 14/715,791 by Cabiri, filed May 19, 2015.
U.S. Appl. No. 14/725,009 by Bar-El, filed May 29, 2015.
Office Action issued May 1, 2015 in U.S. Appl. No. 14/638,525 by Filman.
Office Action issued Jun. 4, 2015 in U.S. Appl. No. 13/667,739 by Cabiri.
Office Action issued Oct. 9, 2013 in IL Application No. 208634.
Office Action issued Nov. 5, 2013 in JP Application No. 2010-527595.
Office Action issued Sep. 29, 2013 in CN Application No. 201080040968.7.
Office Action issued Nov. 4, 2013 in EP Application No. 11 709 234.6.
Office Action issued Nov. 5, 2014 in U.S. Appl. No. 13/643,470 by Alon.
U.S. Appl. No. 14/553,399 by Cabiri, filed Nov. 25, 2014.
Office Action issued Nov. 2, 2014 in CN Application No. 201180006571.0.
Office Action issued Nov. 21, 2014 in U.S. Appl. No. 13/472,112 by Cabiri.
Office Action issued Nov. 21, 2014 in U.S. Appl. No. 13/429,840 by Cabiri.
Int'l Preliminary Report on Patentability issued Nov. 27, 2014 in Int'l Application No. PCT/US2013/039465.
U.S. Appl. No. 13/873,335 by Filman, filed Apr. 30, 2013.
U.S. Appl. No. 13/892,905 by Cabiri, filed May 13, 2013.
U.S. Appl. No. 13/874,121 by Degtiar, filed Apr. 30, 2013.
U.S. Appl. No. 13/874,085 by Cabiri, filed Apr. 30, 2013.
U.S. Appl. No. 13/874,017 by Cabiri, filed Apr. 30, 2013.
Extended European Search Report issued Aug. 7, 2014 in EP Application No. 1417477.4.
Office Action issued Aug. 6, 2014 in EP Application No. 11 707 942.6.
Office Action issued Sep. 2, 2014 in JP Application No. 2012-550069.
Office Action issued Sep. 2, 2014 in JP Application No. 2012-550068.
Office Action issued Aug. 26, 2014 in CN Application No. 201180006567.4.
Int'l Preliminary Report on Patentability issued Oct. 9, 2014 in Int'l Application No. PCT/US2013/033118.
Office Action issued Oct. 9, 2014 in U.S. Appl. No. 13/873,335.
Int'l Search Report and Written Opinion issued Jul. 26, 2013 in Int'l Application No. PCT/US2012/039465.
Int'l Search Report and Written Opinion issued Aug. 5, 2013 in Int'l Application No. PCT/US2013/033118.
U.S. Appl. No. 13/964,651 by Gross, filed Aug. 12, 2013.
Office Action issued Aug. 15, 2013 in CN Application No. 200880117084.X.
Office Action issued Jul. 31, 2015 in U.S. Appl. No. 13/521,181 by Cabiri.
Office Action issued Aug. 13, 2015 in U.S. Appl. No. 14/553,399 by Cabiri.

(56) References Cited

OTHER PUBLICATIONS

Int'l Preliminary Report on Patentability issued Jul. 16, 2015 in Int'l Application No. PCT/US2013/078040.
Notice of Allowance issued Aug. 24, 2015 in U.S. Appl. No. 29/479,307 by Norton.
U.S. Appl. No. 14/258,661 by Cabiri, filed Apr. 22, 2014.
Int'l Search Report and Written Opinion issued Jan. 7, 2014 in Int'l Application No. PCT/US2013/065211.
Office Action issued May 23, 2014 in U.S. Appl. No. 13/472,112 by Cabiri.
U.S. Appl. No. 14/683,193 by Cabiri, filed Apr. 10, 2015.
Office Action issued Feb. 20, 2015 in U.S. Appl. No. 13/521,181 by Cabiri.
Office Action issued Feb. 24, 2015 in U.S. Appl. No. 14/258,661 by Cabiri.
U.S. Appl. No. 14/638,525 by Filman, filed Mar. 4, 2015.
Extended European Search Report issued Feb. 23, 2015 in EP Application No. 14166596.8.
Office Action issued Mar. 10, 2015 in U.S. Appl. No. 13/643,470 by Alon.
Office Action issued Mar. 10, 2015 in U.S. Appl. No. 12/244,666 by Gross.
Extended European Search Report issued Feb. 23, 2015 in EP Application No. 14166591.9.
Office Action issued Mar. 10, 2015 in CN Application No. 201180006567.4.
Office Action issued Mar. 31, 2015 in JP Application No. 2012-550068.
Office Action issued Jan. 4, 2016 in U.S. Appl. No. 13/892,905 by Cabiri.
Office Action issued Sep. 9, 2015 in U.S. Appl. No. 13/643,470 by Alon.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
Office Action issued Sep. 30, 2015 in U.S. Appl. No. 13/667,739 by Cabiri.
Office Action issued Sep. 18, 2015 in U.S. Appl. No. 13/874,085 by Cabiri.
U.S. Appl. No. 15/196,775 by Cabiri, filed Jun. 29, 2016.
Office Action issued Jul. 7, 2016 in U.S. Appl. No. 13/892,905 by Cabiri.

* cited by examiner

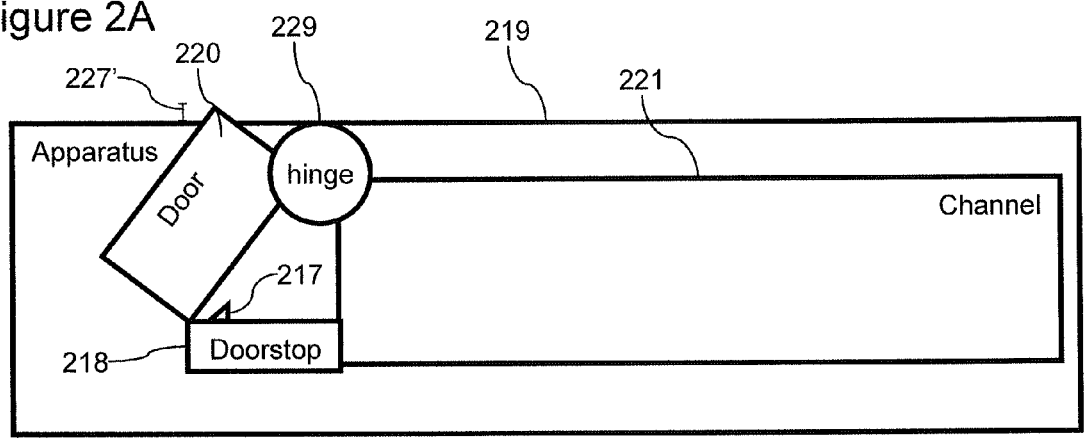
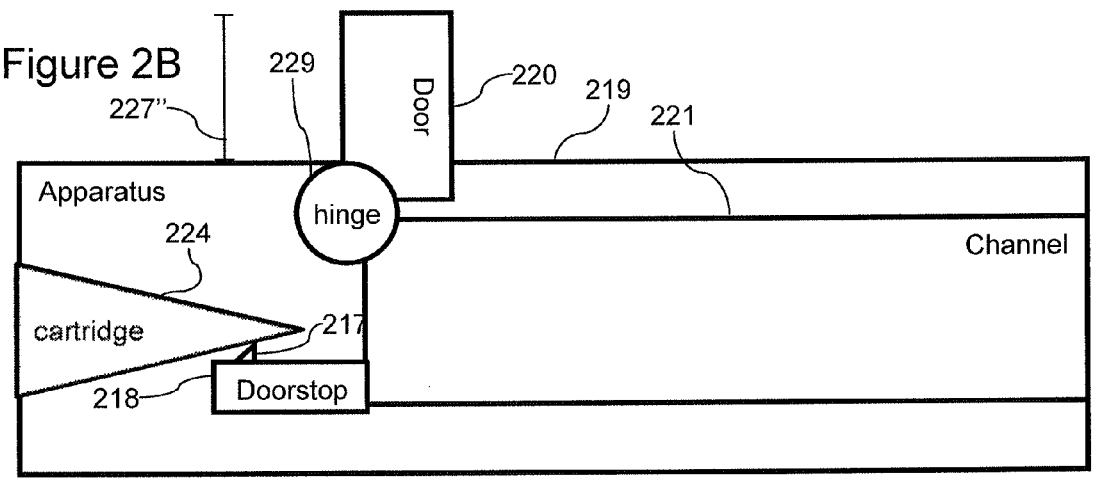
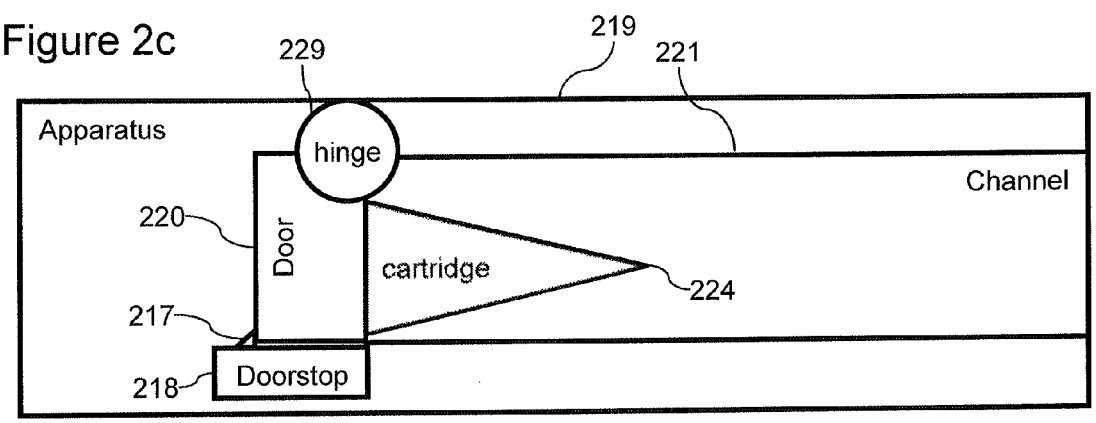

Figure 4A
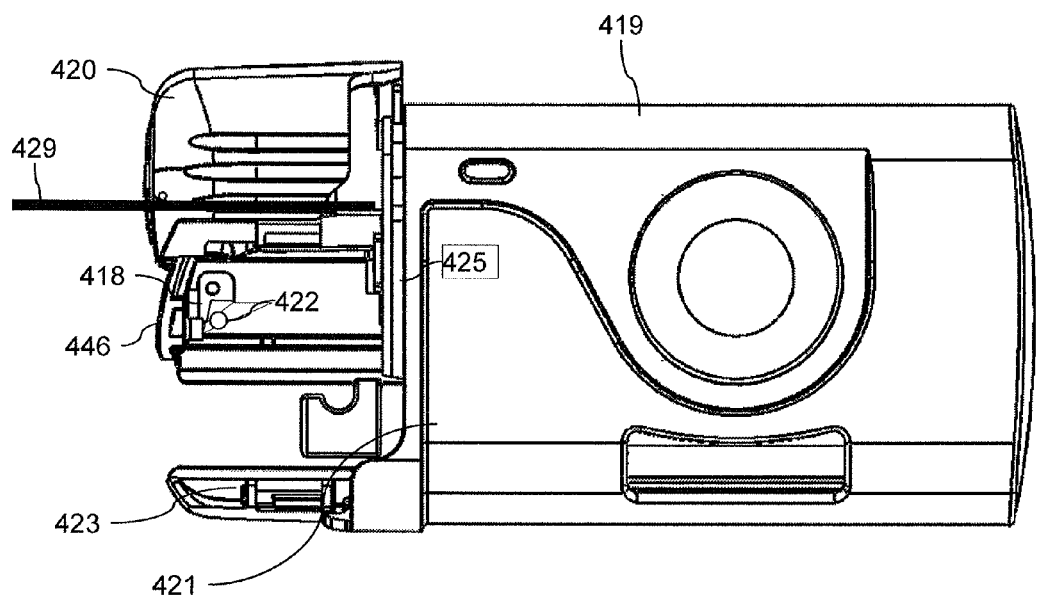
Figure 4B
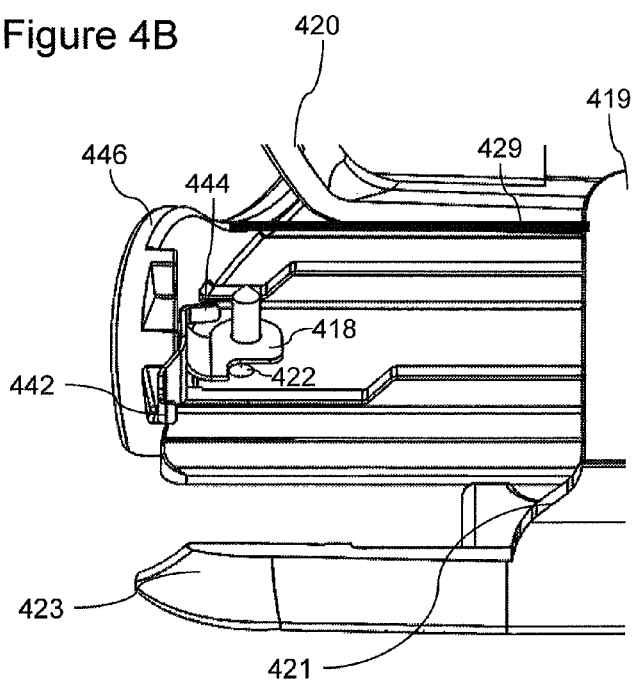
Figure 4C
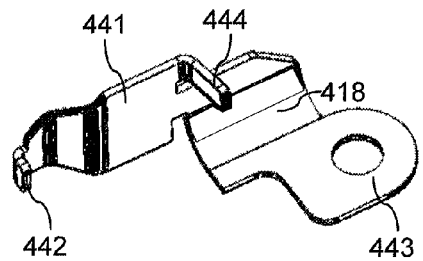
Figure 4C

DOOR AND DOORSTOP FOR PORTABLE ONE USE DRUG DELIVERY APPARATUS

FIELD AND BACKGROUND OF THE INVENTION

The present invention, in some embodiments thereof, relates to a multi-mode door and/or doorstop for a disposable drug delivery apparatus and, more particularly, but not exclusively, to a doorstop that prevents a door of a drug delivery apparatus from locking until a medicine cartridge is inserted.

U.S. Pat. No. 8,157,769 to Cabiri discloses a cartridge insertion assembly including apparatus with a pathway formed therein, a cartridge insertable into the pathway, the cartridge including a cartridge coupling element connectable to an activation mechanism disposed in the apparatus operative to cause a substance contained in the cartridge to be metered out of the cartridge, and a door pivoted to the apparatus that includes a door coupling element arranged with respect to the cartridge such that when the door is in a fully closed mode, the door coupling element couples the cartridge coupling element with a coupling element of the activation mechanism.

U.S. Pat. No. 7,749,194 to Edwards et al. discloses an auto-injector, which can comprise: a vial configured to store and/or contain an injectable medicament, the vial defining a vial longitudinal axis, and a housing comprising the vial. In various embodiments, the injectable medicament can be a medicine, medication, drug, pharmaceutical, prescriptive, agent, antidote, anti-venom, hormone, stimulant, vasodilator, anesthetic, and/or nutritional supplement that is substantially ready for injection.

U.S. Pat. No. 7,588,559 to Aravena et al. discloses an intraosseous injection device including a tool having a distal portion, a proximal portion, and a solution dispensing opening. The distal portion has one or more cutting surfaces. The tool can be coupled with a protective carrier. The tool can be rotatably coupled to a tool actuation mechanism. A housing has a distal end and a proximal end. The housing releasably receives a solution cartridge containing a solution. A solution dispensing mechanism dispenses solution from the solution cartridge. A gripping member grips a proximal portion of the tool. A rotation device rotates the gripping member and thereby rotates the tool about an axis. The proximal portion of the tool connects directly to the solution cartridge such that solution from the cartridge can be delivered through the solution dispensing opening. The tool is configured to rotate relative to the solution cartridge.

United States Patent Application 2009/0093793 to Gross et al. discloses an apparatus for administering a substance to a subject. A vial contains the substance, an inner surface of the vial being shaped to define a protrusion therefrom. A stopper within the vial is slidably coupled to the vial. A first threaded element is (a) rotatable and (b) substantially immobile proximally with respect to the vial during rotation of the first threaded element. A second threaded element is threadedly coupled to the first threaded element. The protrusion impedes rotation of the second threaded element with respect to the vial. The distal end of the second threaded element remains proximal to a distal end of the stopper during rotation of the first threaded element. The first threaded element, by rotating, linearly advances the stopper and the second threaded element toward a distal end of the vial. Other embodiments are also described.

United States Patent Application 2008/0097381 to Moberg et al. discloses a delivery device including, a durable housing portion and a separable disposable portion that selectively engage and disengage from each other. The disposable housing portion secures to the patient-user and may be disposed of after it has been in use for a prescribed period. Components that normally come into contact with a patient-user or with infusion medium are supported by the disposable housing portion, while the durable housing portion supports other components such as electronics and a drive device. A reservoir is supported by the disposable housing portion and has a moveable plunger that operatively couples to the drive device, when the disposable and durable housing portions are engaged.

Additional background art includes U.S. Pat. No. 5,858,001 to Tsals and U.S. Pat. No. 7,967,795 to Cabiri.

SUMMARY OF THE INVENTION

According to an aspect of some embodiments of the present invention there is provided an insertion assembly for a cartridge in a drug delivery apparatus including: an apparatus housing; a channel for insertion of the cartridge formed in the housing; a door to an opening of the channel; a doorstop including a flange and an extension, and wherein the doorstop has two modes, an obstructing mode wherein the flange obstructs closing of the door and wherein the extension extends to a path of insertion of the cartridge into the channel and a non-obstructing mode wherein the door may close unobstructed by the doorstop and wherein, when the cartridge is inserted into the channel, the cartridge engages the extension moving the doorstop to the non-obstructing mode.

According to some embodiments of the invention, the doorstop includes a base, and the flange is held above the base in the obstructing mode, such that when the door rests on the flange the door protrudes from the housing by a predetermined distance.

According to some embodiments of the invention, the doorstop includes a rotating base and wherein the doorstop rotates from the obstructing mode to the non-obstructing mode.

According to some embodiments of the invention, the doorstop includes a sliding base and wherein the doorstop slides from the obstructing mode to the non-obstructing mode.

According to some embodiments of the invention, in the non-obstructing mode the doorstop blocks an exit of the channel, impeding removal of the cartridge from the channel.

According to some embodiments of the invention, the cartridge includes a flange and the engaging is by the cartridge flange.

According to some embodiments of the invention, the door has at least three states: a fully open state wherein the door clears an opening to the channel enough to allow insertion of a cartridge into the channel and wherein in the fully open state the door protrudes from the apparatus, a transport state wherein the door at least partially obstructs the opening and wherein in the transport state the door protrudes from the apparatus less than the protruding during the open state, and a fully closed state wherein the door obstructs the opening enough to prevent both insertion and removal of the cartridge through the opening; and wherein the door moves freely between the transport state and the fully open state.

According to some embodiments of the invention, the door includes a notch on an inside surface thereof, the notch supporting a projection from the cartridge when the door is in the closed state.

According to some embodiments of the invention, the door is mounted on a pivot and wherein the door pivots between the states.

According to some embodiments of the invention, the door includes a coupler, the coupler located such that in when the door is in the closed state the coupler couples a movable element of the cartridge to a motive element in apparatus.

According to some embodiments of the invention, the assembly further includes a latch and wherein, in the fully closed state the latch reversibly latches the door.

According to some embodiments of the invention, the assembly further includes a latch and wherein, in the closed state the latch permanently locks the door.

According to some embodiments of the invention, in the permanently locked state the door is latched to the doorstop in the non-obstructing mode.

According to some embodiments of the invention, the assembly further includes a hook mounted to the doorstop and wherein latching is to the hook.

According to some embodiments of the invention, the assembly further includes a stabilizer maintaining the doorstop in the obstructing mode, until a force greater than a threshold value moves the doorstop into the non-obstructing mode.

According to an aspect of some embodiments of the present invention there is provided a method of preparing a drug delivery apparatus for use the apparatus including a housing having a insertion channel and a cartridge configured for insertion into the channel and a door to the channel including: supplying the apparatus in a transport state wherein the door at least partially blocks the channel and wherein a doorstop is in a obstructing mode, obstructing movement of the door into a fully closed state; opening the door; inserting the cartridge and thereby; shifting the doorstop from the obstructing mode into a non-obstructing mode; closing the door, and latching the door.

According to some embodiments of the invention, opening the door increases a protrusion of the door from the housing.

According to some embodiments of the invention, the method further includes supporting a projection from the cartridge on the door when the door is in the closed state.

According to some embodiments of the invention, the opening and closing include pivoting the door in a plane of an opening of the channel.

According to some embodiments of the invention, the method further includes interconnecting a movable element of the cartridge to a motive element of the apparatus by via the closing, wherein the interconnecting is via a coupler mounted to the door.

According to some embodiments of the invention, the latching is temporary.

According to some embodiments of the invention, the method further includes supporting the door on the doorstop in the transport state.

According to some embodiments of the invention, the method further includes impeding by the doorstop of a removal of the cartridge from the channel when the doorstop is in the non-obstructing mode.

According to some embodiments of the invention, the doorstop includes a pin, and wherein upon closing the door with the cartridge inserted, the cartridge displaces the pin.

According to some embodiments of the invention, the latching is to the doorstop. Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2A is a block diagram illustrating a drug delivery apparatus in a travel state;

FIG. 2B is a block diagram illustrating a drug delivery apparatus is an open state;

FIG. 2C is a block diagram illustrating a drug delivery apparatus in a closed state;

FIG. 4A is an overhead view of an exemplary embodiment of a drug delivery apparatus in a fully open state;

FIG. 4B is a perspective view of an exemplary embodiment of a drug delivery apparatus in a fully open state;

FIG. 4C is a detail perspective view of an exemplary embodiment of a doorstop;

DESCRIPTION OF SPECIFIC EMBODIMENTS OF THE INVENTION

Figure 1:
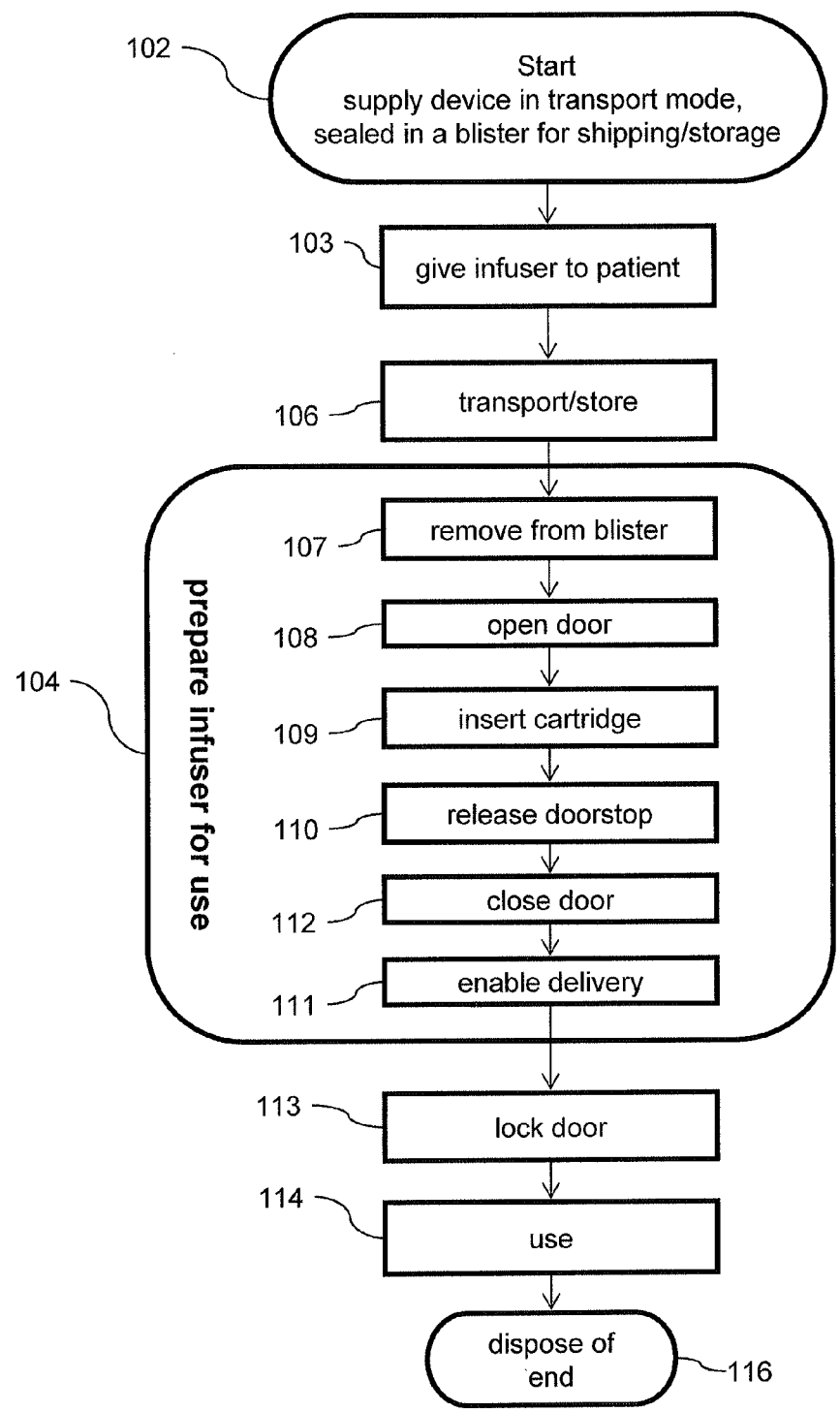
FIG. 1 is a flowchart showing an exemplary embodiment of preparing a drug delivery apparatus for use.

The present invention, in some embodiments thereof, relates to a multi-position door and doorstop for a disposable drug delivery apparatus and, more particularly, but not exclusively, to a doorstop that prevents a door of a drug delivery apparatus from locking until a medicine cartridge is inserted.

Overview

3 State Door

An aspect of some embodiments of the current application is a doorstop to a drug delivery apparatus that encourages a user of the apparatus to perform the proper usage steps in the proper order. For example, a user may be expected to receive an injector in a transport state, open it to an open state, insert a cartridge, and/or close the cartridge before operation. In some cases the user of the apparatus may be anxious, distracted and/or confused and/or disabled. A doorstop may optionally be provided to make the performing the proper steps in the proper order intuitive, simple and/or easy. The doorstop may also deter the user from performing an incorrect action and/or the doorstop may also deter the user from performing an action in an improper order.

Transport State

In some embodiments a delivery apparatus may be supplied to a patient in a transport state configured for transport and/or storage. In the transport state the apparatus may optionally be configured to be compact and/or to resist damage for example from rough handling. For example, in a transport state, a door of the delivery apparatus may be configured to not protrude from the housing of the apparatus and/or to protrude very little from the housing of the apparatus. A protruding part may sometimes cause an apparatus to be non-compact. A protruding part may sometimes be vulnerable to damage. For example, in the transport state, the door may optionally protrude from the housing of the delivery apparatus less than 4 mm and/or less than 2 mm. As used herein, the length of a protrusion of a door from an apparatus means the distance from the point on the door furthest from the apparatus to the closest point on the apparatus.

In some embodiments, in the transport state, a doorstop may be provided in an obstructing mode. In the obstructing mode, the doorstop may obstruct closing of the door. For example, in the obstructing mode, the doorstop may obstruct premature closing of the door for example due to vibrations and/or rough handling and/or inadvertent closing by a confused patient.

In some embodiments, prior to use of a delivery apparatus, a user may be open a door. For example, in the transport mode the door may fully and/or partially block a cartridge channel. Optionally in order before inserting a cartridge into the channel, the user may open the door. The door may optionally move easily and/or intuitively from the transport state to an open state. For example, in the transport state the door may protrude slightly from the apparatus. In the transport state, the door may for example protrude between 0.1 and 0.8 cm. The slight protrusion of the door may help an anxious and/or confused patient intuitively understand how to open the door.

Open State

In some embodiments, in the open state, a door may clear an opening of a cartridge channel enough to insert a cartridge into the opening. Optionally, in the open state, the door may protrude significantly from the apparatus, for example the door may protrude a distance ranging between 2 and 4 cm. In the open mode the door may protrude for example between 5 and 40 times as much as it protrudes in the transport state.

In some embodiments, while the apparatus is in the open state, the user will insert a cartridge into the cartridge channel. For example, inserting the cartridge may cause a doorstop to move non-obstructing mode. Optionally the doorstop may move into the non-obstructing mode when at least a majority of the cartridge has been inserted into the channel. For example, the doorstop may move into the non-obstructing mode when the cartridge has been inserted to a degree ranging been 60% and 100% of its fully inserted position. In the non-obstructing mode, the doorstop may optionally impede removal of the cartridge from the channel. For example insertion of the cartridge may optionally cause priming of the apparatus, for example by puncturing a septum. Optionally it may be undesirable to remove the cartridge after insertion.

Closed State

In some embodiments, moving the doorstop into the non-obstructing mode may allow the door to close and/or permanently lock. In a closed state, the door may optionally inhibit removal, corruption, misuse, and/or reuse of the cartridge and/or the delivery apparatus. Alternatively and/or additionally in a closed state the door may inhibit dirt and or infecting organisms from entering the delivery apparatus. Alternatively and/or additionally in the closed state the door may inhibit a person from being injured by the delivery apparatus. Alternatively or additionally, in a closed state the door may protect the delivery apparatus from tampering and/or insertion of foreign objects. Optionally, the apparatus may be configured non-operable until the door is closed.

In some embodiments, a doorstop may prevent opening of a door when the door is closed after insertion of a cartridge. For example, a doorstop may be latch the door to the housing of the apparatus and/or a latch may attach to the doorstop when the doorstop is in the non-obstructing mode.

In some embodiments, the housing of a drug delivery apparatus may include a supporting structure. The supporting structure may optionally engage the door and/or support the door when the door is in the closed state and/or the transport state and/or a permanently locked state.

In some embodiments, a coupler may be mounted on the door. The coupler may optionally transmit power from the drug delivery apparatus to the cartridge when the door is in a closed mode. Optionally, the power may be used to deliver the drug. Optionally, in a closed state and/or locked state, the door may support a component of the drug delivery apparatus. For example, the door may optionally include a notch to support a projection from said cartridge. For example, the door may support a rear end of the cartridge. Optionally the projection may revolve in the notch. Optionally, when in a closed state and/or in a locked state, the door may serve as a counter force. For example, the door may act as a counter force for pushing a plunger into a syringe to deliver the drug.

In some embodiments the door may pivot. For example, the door may pivot in the plane of the opening of the cartridge channel. Alternatively or additionally, the door may slide. For example, the door may slide in the plane of the opening. Alternatively or additionally, the door may swing. For example, the door may swing on a hinge into and out of the plane of the opening.

Detailed Embodiments

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Method of Preparing a Drug Delivery Apparatus

FIG. 1 is a flow chart illustrating an exemplary embodiment of a method of preparing a drug delivery apparatus for use. For example, the delivery apparatus may be supplied in a transport state to a user. Optionally, the user may open the delivery apparatus, insert a cartridge and close a door. Optionally, the apparatus may be designed to encourage proper carrying out of the preparatory steps in the proper order and/or to inhibit improper actions and/or actions in the wrong order. For example, a doorstop may optionally be provided in an obstructing mode. In the obstructing mode the doorstop may optionally obstruct premature closing of a door. Optionally, inserting a cartridge may move the doorstop from the obstructing mode to a non-obstructing mode. In the non-obstructing mode, the doorstop may optionally allow closure of the door. Alternatively and/or additionally, in the non-obstructing mode, the doorstop may impede removal of the cartridge.

Referring now to FIG. 1, in some embodiments a drug delivery apparatus may be supplied 102 in a transport state in a sealed blister. The blister may protect the apparatus from contamination. The apparatus may be given 103 to the user in the sealed blister.

In some embodiments, the user may transport 106 the apparatus (for example a patient may take the apparatus home) and/or store the apparatus. For the sake of transport 106 and/or storage, the apparatus may be optionally placed in a transport state without large projecting parts that take up space and/or are vulnerable to breakage. For example, in the transport mode, the door may rest on a doorstop so that the door is almost closed. Alternatively or additionally, the apparatus may be transported and/or stored before being given to the patent.

Before use, the user may optionally prepare 104 the apparatus for use. For example, the user may take the apparatus out 107 from its protective blister. In some cases, when opening a blister to take out 107 the apparatus a user may apply significant force. The transport mode of the apparatus may optionally be configured to prevent breakage of the apparatus while opening the blister.

In some embodiments, after taking out 107 the apparatus from the blister, a user may open 108 a door of a cartridge channel. Optionally the user may be a patient. Typically a patient may be anxious, confused, feeling sick, have impaired movement, have impaired senses and/or be in pain. Optionally, a delivery apparatus may be designed to allow easy, safe preparation. For example, preparation may be intuitive and/or include safeguards against improper action. Optionally preparation will not include steps, forces and/or noises that may confuse the patient into thinking that there has been a malfunction. Optionally, the apparatus may include reassuring noises and/or forces that reassure the user that he has taken the correct action and/or that the apparatus is working properly. Optionally, opening the door may be an intuitive process. For example, the door may open 108 with minimal smooth application of force (without giving the user the feeling that he is forcing and/or breaking something). Optionally, a user may be inhibited from performing an act that is not correct and/or not in the correct order. For example, a doorstop may prevent closing 112 of the door before insertion 109 of the cartridge.

In some embodiments, after opening 108 the door, a cartridge is inserted 109 into a channel in the apparatus. Optionally, inserting 109 the cartridge will automatically release 110 the doorstop. For example, the doorstop may be released 110 from the obstructing mode wherein the doorstop obstructs closing 112 of the door to a non-obstructing mode, wherein the door may be closed 112 freely.

In some embodiments, after inserting 109 the cartridge, the user closes 112 the door to the cartridge channel. Optionally, closing 112 the door may enable 111 delivery of the drug. For example, the door may include a coupler. Optionally, when the door is closed the coupler may connect a drive element to a motive element, enabling 111 delivery. Optionally, when the doorstop is in the non-obstructing position, closing 112 the door will cause the door to permanently lock 113. Alternatively or additionally, locking 113 may occur separately from closing 112 the door. For example, locking 113 may occur at some time after closing 112.

In some embodiments, once the door is closed 112 and locked 113 with the cartridge inserted 109 then the apparatus may be used 114. Optionally, after use 114, the sealed apparatus may be safely disposed of 116 for example in the municipal garbage.

Schematic Illustration of an Exemplary Embodiment of a Drug Delivery Apparatus and Doorstop Referring now to the figures, FIGS. 2A-C include block diagrams of three states of a drug delivery apparatus. In some embodiments, a drug delivery apparatus may have at least three states, a transport state, an open state and a closed state. Optionally, the correct or order of preparation of the apparatus may be to open the apparatus from the transport state to the open state. Optionally in the open state a cartridge will be inserted into a cartridge channel. Optionally, after inserting the cartridge, the apparatus will be put into the closed state and used. Optionally the apparatus may include a doorstop. Optionally, in the transport state, the doorstop may serve to support a door in a fully or partially closed position and/or to prevent premature closing of the door before inserting the cartridge. Optionally, inserting the cartridge will release the doorstop and allow closing of the door.

FIG. 2A is illustrates an exemplary embodiment of a drug delivery apparatus 219 in a transport state. A door 220 may optionally be supported by a hinge 229. In the transport state, door 220 may be partially closed and protrude 227' slightly from apparatus 219. In the transport state, door 220 may optionally be inhibited from closing and/or rest on a doorstop 218 in an obstructing mode. Doorstop 218 may optionally include a latch 217. In the transport state door 220 may optionally partially and/or completely obstruct a channel 221.

The transport state, for example as illustrated in FIG. 2A, may have some or all of the following useful properties. Optionally in the transport state apparatus 219 may have a low profile and/or resist breaking, for example because there may be no parts that protrude significantly from apparatus 219. In the transport mode it may optionally be simple and intuitive to open the door, for example, because the door is already partially open and/or because there is no significant resistance to further opening the door. In the transport mode, doorstop 218 may obstruct the door from accidental closing, for example due to vibration during transport, rough handling and/or a human error.

In some embodiments, before employing apparatus 219, a user may open door 220 into an open configuration, for example as illustrated in FIG. 2B. In the open configuration, door 220 may optionally clear channel 221 enough to insert a cartridge 224 into channel 221. Doorstop 218 and cartridge 224 may optionally be configured such that inserting cartridge 224 moves doorstop 218 from a obstructing mode, for example as illustrated in FIGS. 2A,B, into a non-obstructing mode, for example as illustrated in FIG. 2C. In the open mode, door 220 may protrude 227" significantly from apparatus 219. Optionally, once cartridge 224 has been fully and/or partially inserted into channel 221, latch 217 may inhibit a user from retracting cartridge 224 back out of channel 221.

In some embodiments, after inserting cartridge 224, the user may close door 220, putting apparatus 219 into a closed mode, for example as illustrated in FIG. 2C. In the closed mode, door 220 may optionally fully and/or partially block the opening of channel 221. Optionally, in the closed mode, latch 217 may permanently and/or temporarily lock door 220.

States of a Drug Delivery Apparatus

Figure 3:
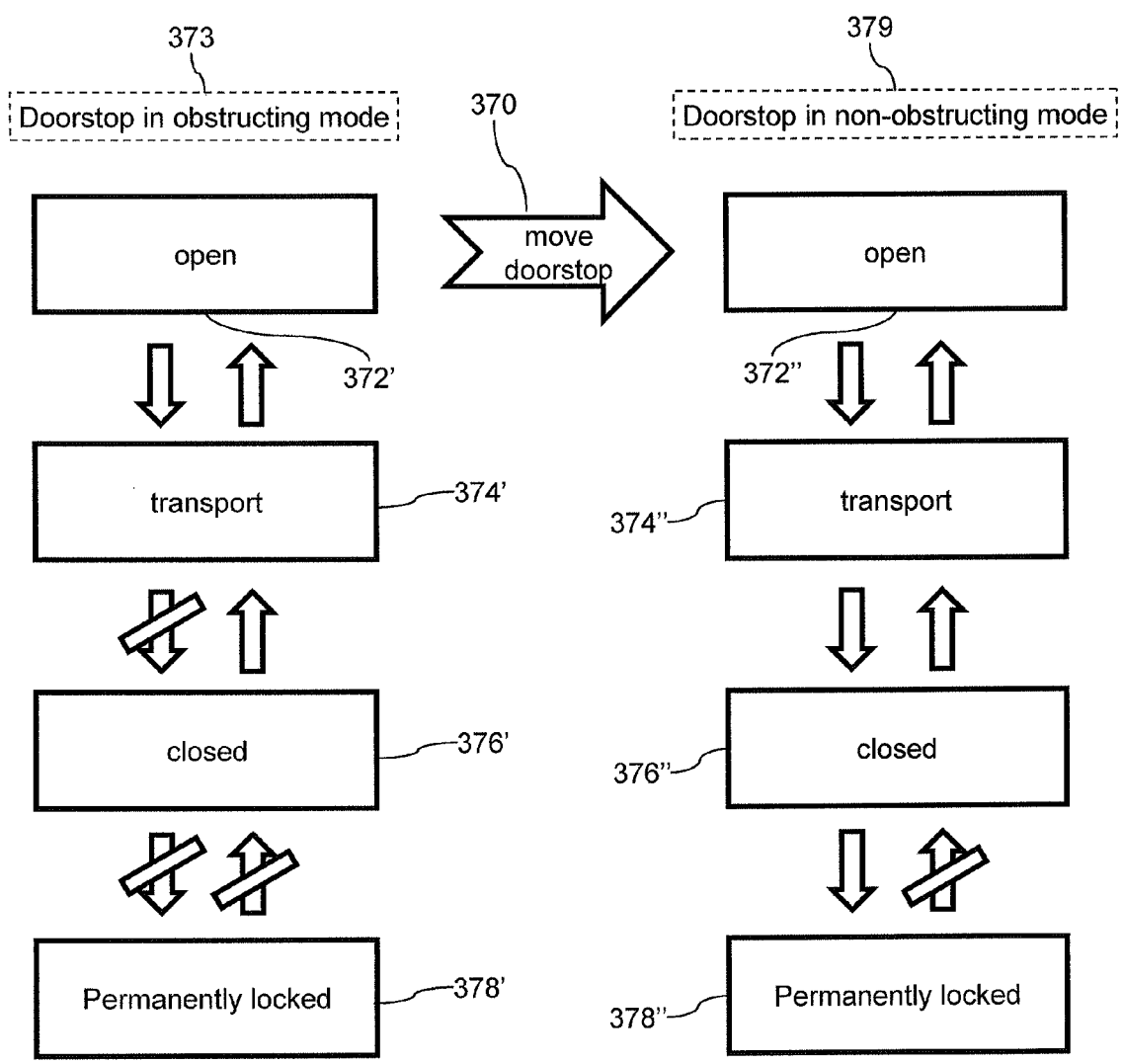
FIG. 3 is a state diagram illustrating exemplary states of a drug delivery apparatus.

Referring now to the figures, FIG. 3 is a state diagram illustrating states of an exemplary embodiment of a drug delivery apparatus. In some embodiments a doorstop will have at least two modes: an obstructing mode, where the doorstop obstructs closing and/or locking of a door, and a non-obstructing mode, wherein the doorstop does not obstruct closing and/or locking of the door. Optionally in the non-obstructing mode, the doorstop may impede removal of a cartridge and/or lock the door closed. Optionally, the drug delivery apparatus may have three modes: an open mode, a transport mode and/or a closed mode. Optionally, the closed mode may be permanent and/or temporary. Alternatively or additionally, the apparatus may have a fourth mode, a permanently locked mode. Alternatively or additionally, the apparatus may have more modes.

In some embodiments, a drug delivery apparatus may be supplied to a user in a transport state 374' with the doorstop in an obstructing mode 373. The user may optionally open the door to an open state 372'. The door may optionally move freely between transport state 374' and open state 372'. With the doorstop in the obstructing mode 373, the apparatus may optionally be obstructed from moving to a closed state 376'. With the doorstop in the obstructing mode, the apparatus may optionally be obstructed from moving to a locked state 378'. Optionally, when the apparatus is in transport state 374' and/or open state 372' the apparatus may be prevented from delivering the drug.

In some embodiments, if by some means, a user forces the apparatus into closed state 376' while the doorstop is in obstructing mode 373, the door may be able to return to transport state 374' and/or open state 372'. Optionally, with the doorstop in the obstructing mode 373, the door may return spontaneously from closed state 376' to transport state 374' and/or open state 372'. Alternatively or additionally, there may be a temporary latch which can be released by the user to return the door from closed state 376' to transport state 374'.

In some embodiments, a cartridge may be inserted into the apparatus. For example, the cartridge may be inserted while the apparatus is in the open state. Optionally, inserting a cartridge into the delivery apparatus may move 370 the doorstop from obstructing mode 373 to a non-obstructing mode 379. Optionally, when the doorstop is in non-obstructing mode 379, removal of the cartridge may be impeded.

In some embodiments, the doorstop may be stable and/or bi-stable. For example, the doorstop may be prevented from moving spontaneously from the obstructing mode 373 to non-obstructing mode 379. Alternatively or additionally it may be prevented from moving spontaneously from non-obstructing mode 379 to obstructing mode 373. Optionally, movement of doorstop may be one direction, for example once in the non-obstructing mode 379 it may remain there permanently and not return to obstructing mode 373. Alternatively or additionally the doorstop may not be stabilized.

With the doorstop in the non-obstructing mode 379, the apparatus may optionally be able to move from open state 372" and/or transport state 374" to a closed state 376". With the doorstop in the non-obstructing mode 379, the apparatus may optionally be able to move to a locked state 378". Optionally, unless the apparatus is in the closed state 376" and/or locked state 378" the apparatus may be prevented from delivering the drug. Optionally, when the apparatus is in the closed state 376" and/or locked state 378" the apparatus may deliver the drug.

In some embodiments, after a user place the apparatus into closed state 376" while the doorstop is in non-obstructing mode 379. Optionally, the door may be able to return from closed state 376" to transport state 374" and/or open state 372". Alternately or additionally, with the doorstop in the non-obstructing mode 379, the doorstop may obstruct the door from returning from closed state 376" and/or there may be a temporary latch which can be released by the user to return the door from closed state 376" to transport state 374". While the doorstop is in non-obstructing mode 379, the door may optionally be moved to a permanently locked state 378".

Detailed Exemplary Embodiment of a Drug Delivery Apparatus and Doorstop

Referring now to the figures, FIGS. 4-11 illustrate a detailed exemplary embodiment of a drug delivery apparatus. The apparatus of FIGS. 4-11 optionally includes a door that pivots open and closed parallel to the plane of the opening to a cartridge channel. Optionally the apparatus includes a doorstop. Optionally, in a transport state the doorstop is in an obstructing mode. Optionally, in the transport state, the door is nearly closed and rests on the doorstop. Optionally, with the doorstop in an obstructing mode, the door is obstructed from closing. Optionally, opening the door allows inserting a cartridge.

In some embodiments, inserting a cartridge into the apparatus switches the doorstop into a non-obstructing mode. Optionally, the switching is by rotating the doorstop. In the non-obstructing mode, the doorstop optionally impedes removal of the cartridge. In the non-obstructing mode, the door is optionally allowed to close and permanently lock.

An optional coupling may be mounted to the door. When the door is in the closed and/or locked state, the coupling may link a motive element of the drug delivery apparatus to a movable element of the cartridge. Optionally, when linked to the motive element, the movable element may instigate delivery of the drug.

In some embodiments, when the door is closed it may serve as a counter force for an expanding plunger to deliver the medicine. Alternatively, when permanently closed, the door may protect the apparatus from tampering and/or protect the apparatus from reuse and/or misuse and/or protect the user for injury from internal parts of the apparatus.

Referring now to the figures, FIG. 4A is an overhead view of an exemplary embodiment of a drug delivery apparatus including a housing 419 and a door 420 in a fully open state. A doorstop 418 is shown in an obstructing mode. Door 420 optionally pivots around an axis 429. Optionally while pivoting door 420 remains parallel to the opening of a cartridge channel 421. A latch 423 is optionally provided to secure door 420 when it closes.

Figure 11A:
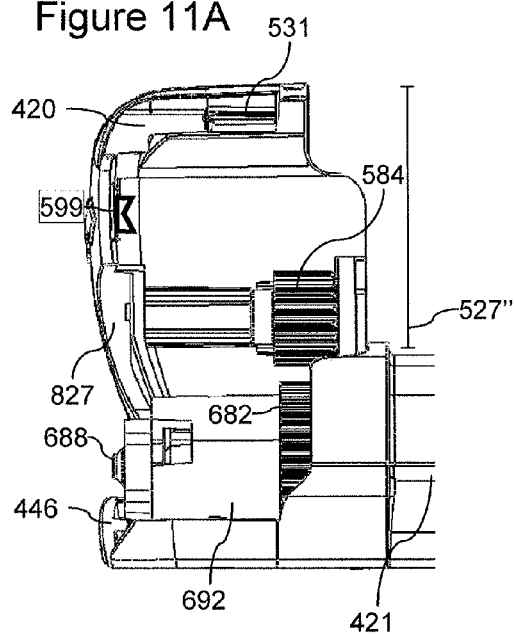
FIG. 11A is a detail side view of an exemplary embodiment of a drug delivery apparatus in an open state showing a movable element of a cartridge and a coupler.
Figure 11B:
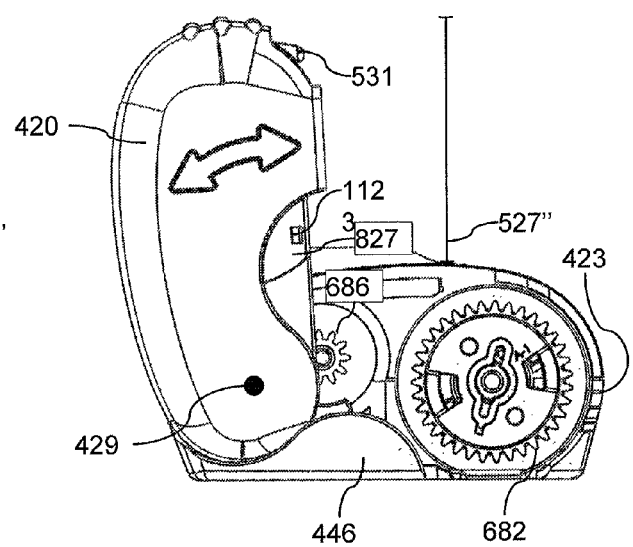
FIG. 11B is a detail rear view of an exemplary embodiment of a drug delivery apparatus in an open state showing a movable element of a cartridge and a motive element of the drug delivery apparatus.
Figure 11C:
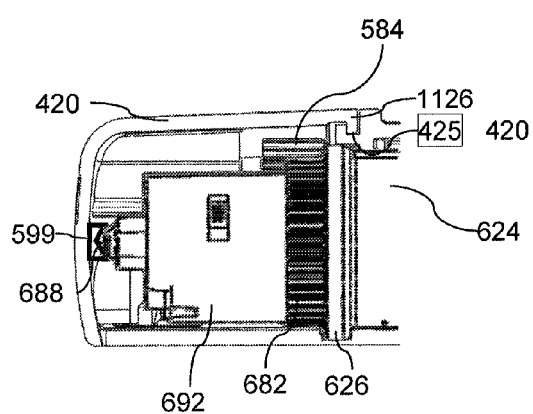
FIG. 11C is a detail side cutaway view of an exemplary embodiment of a drug delivery apparatus in a closed state showing a movable element of a cartridge and a coupler.

In some embodiments, (for example as illustrated in FIG. 11C) when door 420 is closed it may optionally serve as a counter force and/or a support for a mechanism, for example for a plunger mechanism to eject a medicine. Support may optionally be supplied to door 420 in the closed state by a rear support 446 and/or a groove 425.

In some embodiments, a stabilizer 422 may provide bi-stability to doorstop 418. For example, in FIG. 4A, stabilizer 422 may include a nubble. Doorstop 418 may cross over the nubble to move from the obstruction mode to the non-obstructing mode. For example, in FIG. 4A, stabilizer 422 holds doorstop 418 in the obstruction mode. In order to move doorstop 418 from the obstruction mode into the non-obstruction mode optionally entails a force to rotate doorstop 418 over stabilizer 422. For example, as the cartridge is fully inserted passing stabilizer 422 may give the user a reassuring feeling of doorstop 418 clicking into place. Optionally, when doorstop 418 is in the non-obstruction (for example see FIG. 9) a force may be entailed to rotate doorstop 418 over stabilizer 422 into the obstruction mode. For example, stabilizer 422 may prevent vibrations (for example during transport and/or handling) from moving doorstop 418 out of a desired mode.

Referring now to the figures, FIG. 4B is a perspective view an exemplary embodiment of a drug delivery apparatus with door 420 in a fully open state. In FIG. 4B, optional details of doorstop 418 are illustrated. For example, doorstop 418 includes a flange 444 to obstruct door 420. Optionally, in the transport mode, door 420 rests on flange 444. Optionally, rear support 446 prevents door 420 from passing behind flange 444, for example circumventing doorstop 418.

In some embodiments, doorstop 418 may include a spacer 442. For example, when doorstop is in the non-obstructing mode (for example see FIG. 9) spacer 442 may stick out into the exit path of the cartridge. If a user tries to remove a cartridge while doorstop 418 is in the non-obstructing mode, the cartridge may optionally collide with spacer 442 rotating doorstop 418 toward the obstructing mode and impeding removal of the cartridge.

Referring now to the figures, FIG. 4C, shows a close up perspective of the exemplary embodiment of doorstop 418, flange 444 and spacer 442. Doorstop 418 includes for example a rotating base 443. An extension 441 is optionally bent according to the inner surface of door 420. The bent shape of extension 441 holds, for example, flange 444 in a closing path of door 420. In the obstructing mode, extension 441 projects into the path of the cartridge entering channel 221. For example, in the obstructing mode, extension 441 bends along the inner edge of door 420, projecting into the beginning of the path of the cartridge. Extension 441 optionally has a twisted shape that distances flange 444 above base 443. The protrusion of door 420 is the transport mode may optionally result, in part, from the distance of flange 444 above base 443.

Figure 5A:
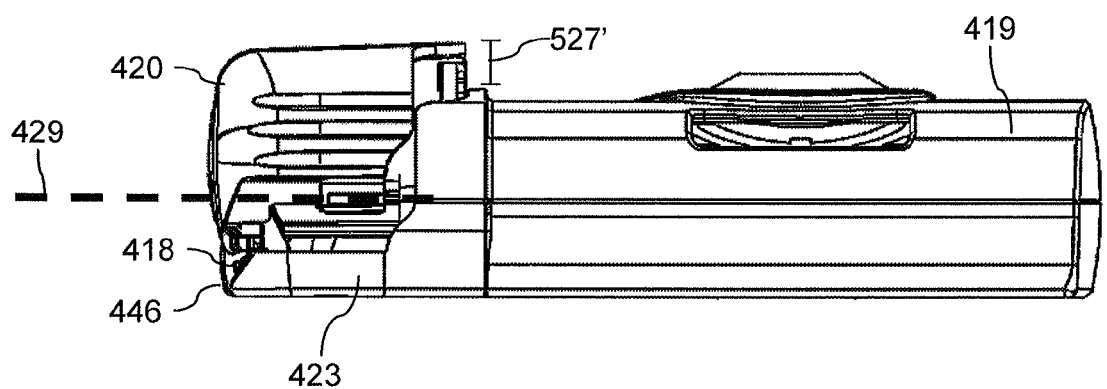
FIG. 5A is a schematic side view of a drug delivery apparatus in a transport state.
Figure 10:
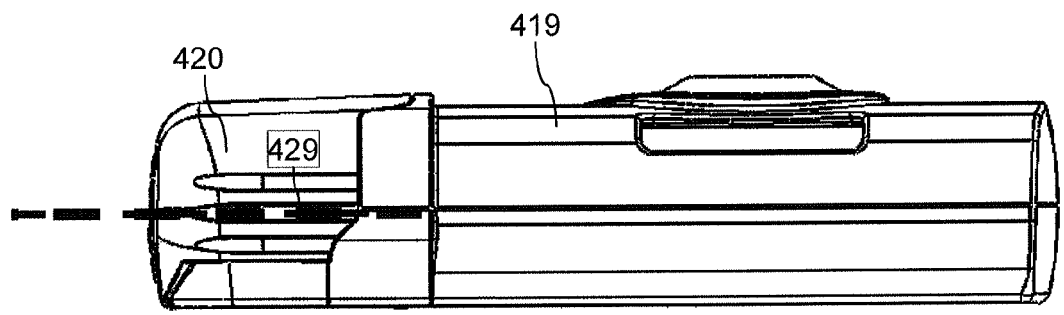
FIG. 10 is a schematic side view of a drug delivery apparatus in a fully closed state, ready for use.

Referring now to the figures, FIG. 5A illustrates side view of exemplary drug delivery apparatus housing 419 in a transport state. In the exemplary embodiment of FIG. 5A, in the transport state, door 420 rests on doorstop 418. For example doorstop 418 holds door 420 a few millimeters above its closed state (for example as illustrated in FIG. 10). Optionally, in the transport state door 420 protrudes 527' a few millimeters above housing 419. The slight protrusion may, for example, help a user to understand how and where to open door 420.

Figure 5B:
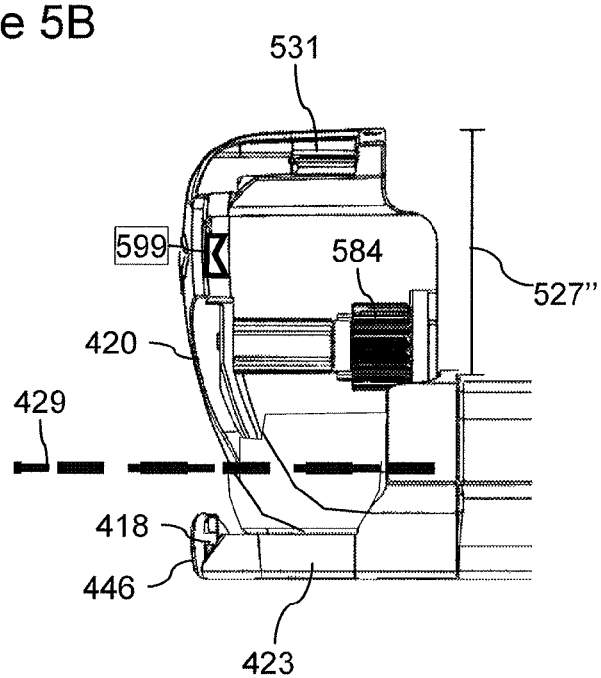
FIG. 5B is a schematic side view of a drug delivery apparatus in a fully open state.

FIG. 5B is a side view illustration of door 420 in an open state. In the example of FIG. 5B, in the open state, door 420 protrudes 527" considerably more than in the transport mode (as illustrated, for example, in FIG. 5A). Also seen in FIG. 5B are an optional coupler 584 and an optional hub 599. An exemplary embodiment of coupler 584 will be explained in the text accompanying FIG. 11. An exemplary embodiment of a hub 599 will be explained in the text accompanying FIG. 11. An optional hook 531 to grasp latch 423 is illustrated in FIG. 5.

Figure 6:
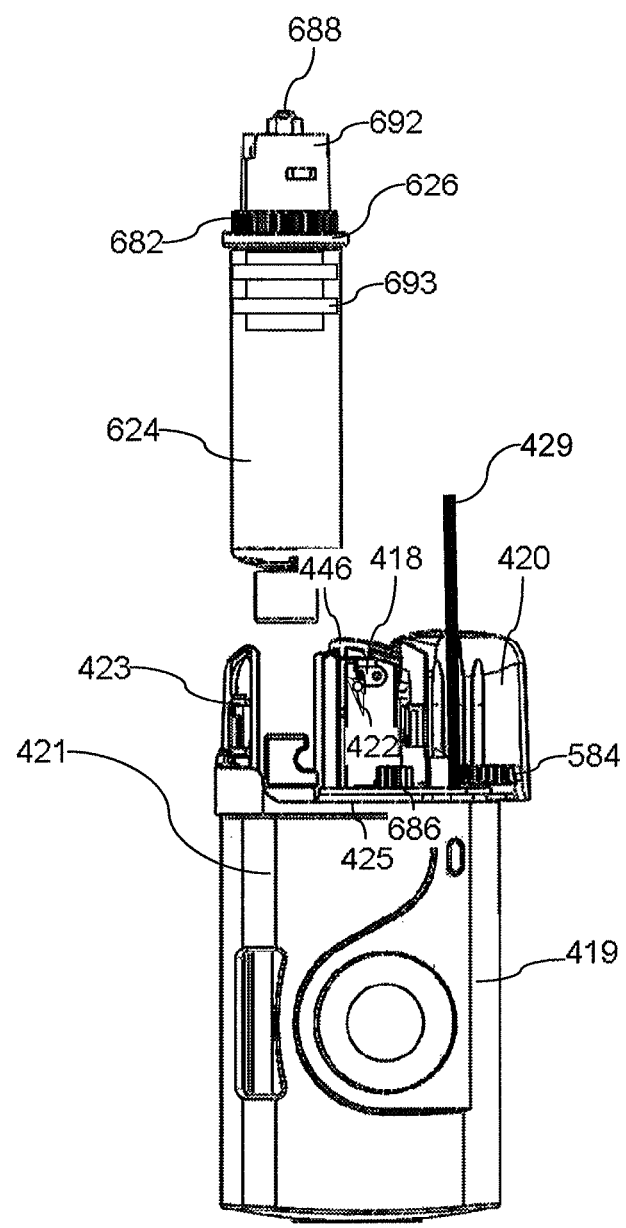
FIG. 6 is an overhead view of an exemplary embodiment of a drug delivery apparatus in a fully open state with a cartridge ready to insert.

Referring now to the figures, FIG. 6 illustrates an overhead view of an exemplary embodiment of a drug delivery apparatus. In FIG. 6, an exemplary embodiment of an optional cartridge 624 is illustrated. In FIG. 6, cartridge 624 is shown ready for insertion into channel 421.

In some embodiments, cartridge 624 is in the form of a syringe barrel. Optionally, cartridge 624 includes a flange 626. Flange 626 may be, for example, similar to flanges on standard syringes. For example, flange 626 may be at or towards the rear end (opposite the tip) of the syringe.

In some embodiments, an optional telescoping assembly 692 may be supplied. Assembly 692 may optionally be fitted to the open end of cartridge 624. Telescoping assembly 692 may optionally be driven by a movable element 682 which may, for example, include a gear. Optionally, the gear revolves telescoping assembly 692. Optionally when door 420 is closed, coupler 584 connects movable element 682 to a motive element 686 (for example see FIG. 11D). Motive element, 686 may optionally supply torque to drive movable element 682. Assembly 692 may include a projection 688. For example, projection 688 may be configured to fit in a notch in door 420 (for example hub 599 of FIG. 11C). Optionally, projection 688 may fit into hub 599 when door 420 is closed. When projection 688 is fit into hub 599, projection 688 may optionally support the rear end of assembly 692. When movable element 682 revolves, projection 688 may optionally revolve in the hub 599. Telescoping assembly 692 may optionally drive a plunger 693. Plunger 693 may, for example, be driven by telescoping assembly 692 into cartridge 624 to deliver a drug.

Figure 7:
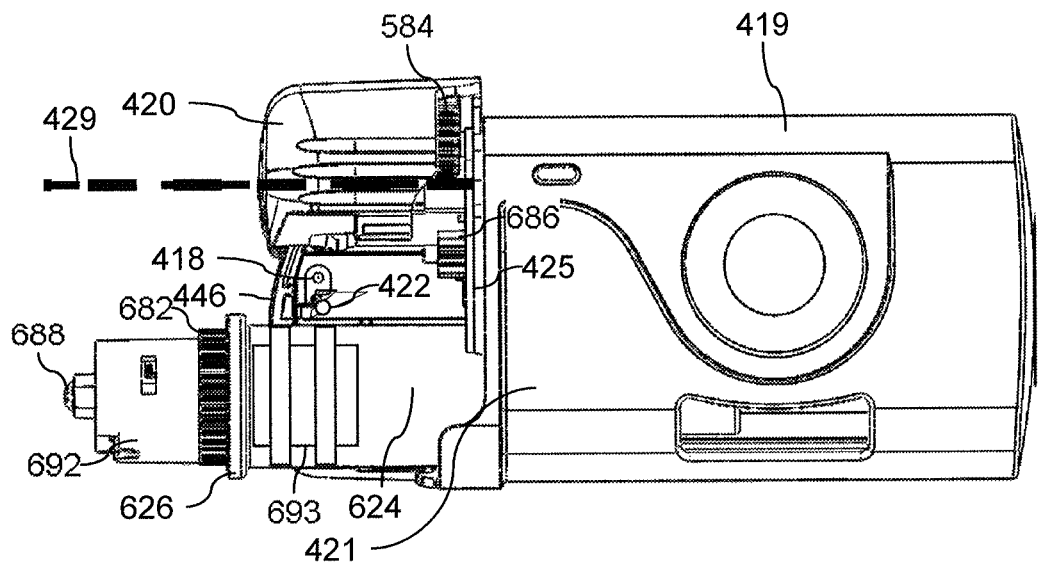
FIG. 7 is an overhead view of an exemplary embodiment of a drug delivery apparatus in a fully open state with cartridge partially inserted.

Referring now to the figures, FIG. 7 illustrates an overhead view of an exemplary embodiment of a drug delivery apparatus. In FIG. 7, an exemplary embodiment of an optional cartridge 624 is illustrated in a partially inserted position.

In some embodiments, the sides of cartridge 624 optionally do not contact doorstop 418 while cartridge 624 is being inserted. This may have a few advantages. For example, if cartridge 624 can be removed from the partially inserted position of FIG. 7, doorstop 418 remains in the obstruction mode. For example, no irreversible changes have taken place. For example, if there is a label on cartridge 624 it will not be scratched by doorstop 418. For example, a user inserting cartridge 624 will not be subject to an annoying scratching sensation as he inserts the cartridge. Along with possible being annoying, the scratching sensation may in some cases cause a user to believe that he made a mistake and/or that the apparatus is not working properly.

Figure 8A:
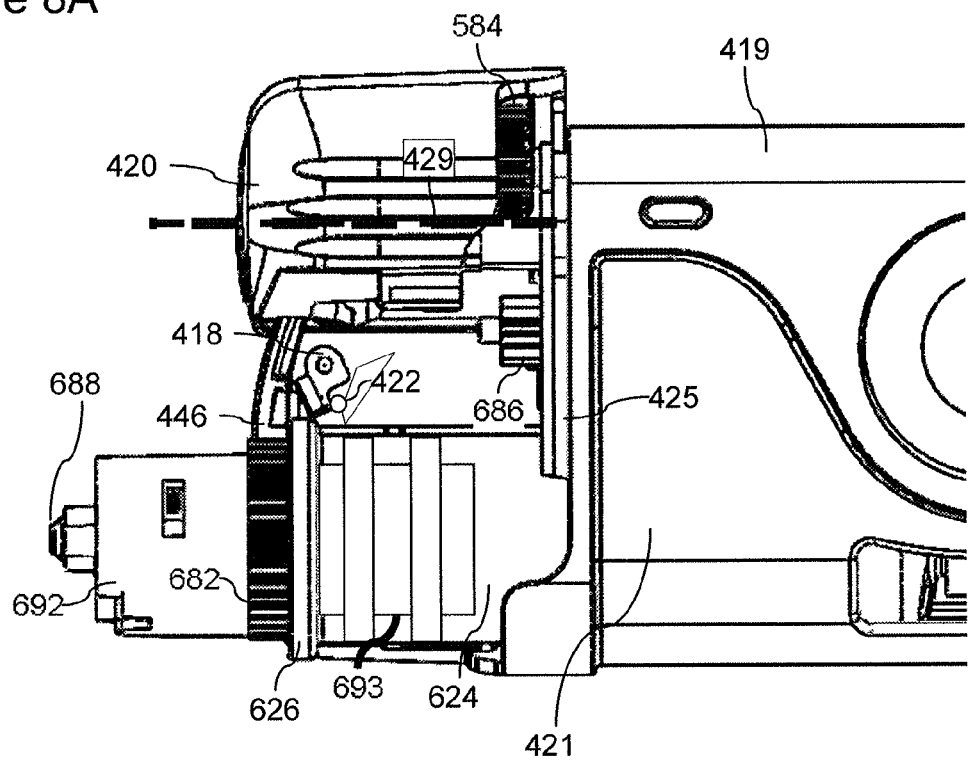
FIG. 8A is an overhead view of an exemplary embodiment of a drug delivery apparatus in a fully open state with a cartridge moving the doorstop from a obstructing mode to a non-obstructing mode.
Figure 8B:
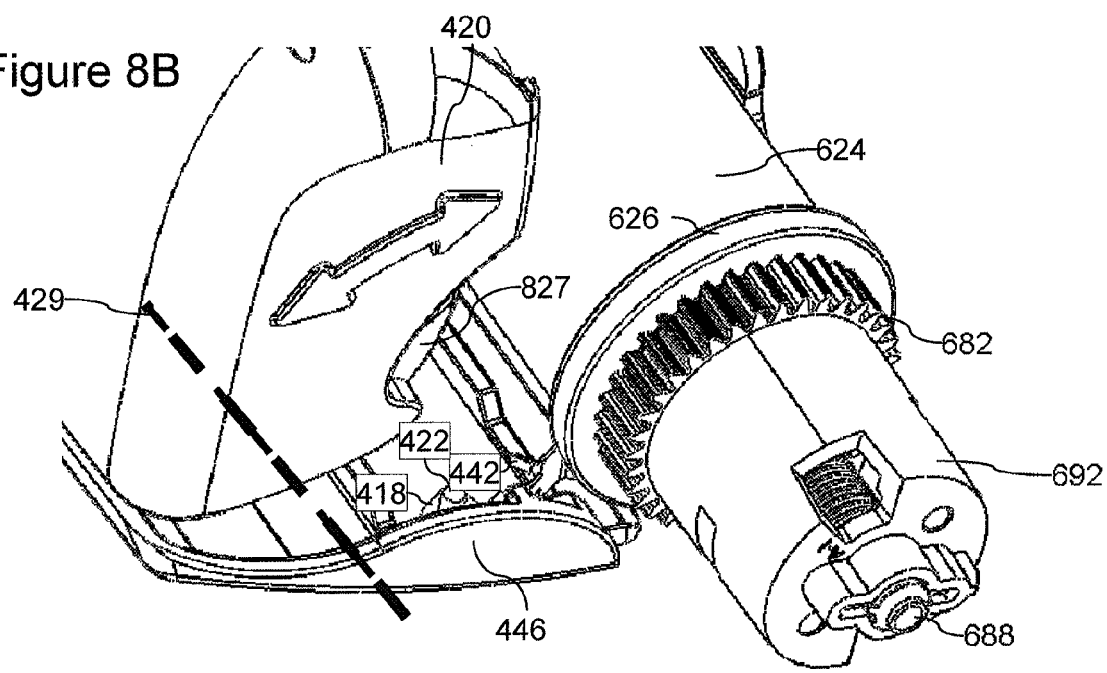
FIG. 8B is a perspective view of an exemplary embodiment of a drug delivery apparatus in a fully open state with a cartridge moving the doorstop from a obstructing mode to a non-obstructing mode.

Referring now to the figures, FIGS. 8A,B illustrate overhead and perspective views respectively of an exemplary embodiment of a drug delivery apparatus with a cartridge inserted to a point at which it begins to switch doorstop 418 from the obstructing mode to the non-obstructing mode. Optionally, cartridge 624 will switch doorstop 418 to non-obstructing mode just before an irreversible process. For example, doorstop 418 may be switched from the obstructing mode to the non-obstructing mode right before the front end of cartridge 624 reaches a needle that pierces a septum. Optionally, in the non-obstructing mode, doorstop 418 may impede removal of cartridge 624. Optionally, switching doorstop 418 to the non-obstructing state will impede removal of cartridge 624 once the septum is pierced.

In some embodiments, a flange 626 will contact doorstop 418 to rotate it and switch it to the non-obstructing state. Flange 626 may optionally shield movable element 682 from contact and/or damage from doorstop 418. For example, flange 626 moves doorstop 418 into the non-obstructing mode when the tip of cartridge 624 has been inserted to about 60% its final position.

In some embodiments, door 420 may include a feature to engage a structural support in a closed position. The structural support may, for example be a part of the delivery apparatus housing 419. For example, door 420 may include an indentation 827 that engages with rear support 446 upon when door 420 is in a closed state. Optionally, indentation 827 may fully and/or partially engage rear support 446 when door 420 is in the transport state. Engaging rear support 446 strengthens door 420 for example to prevent breakage by outside forces and/or to prevent door 420 from passing behind flange 444 circumventing doorstop 418 and/or to provide support for hub 599, projection 688 and/or telescoping assembly 692.

Figure 9:
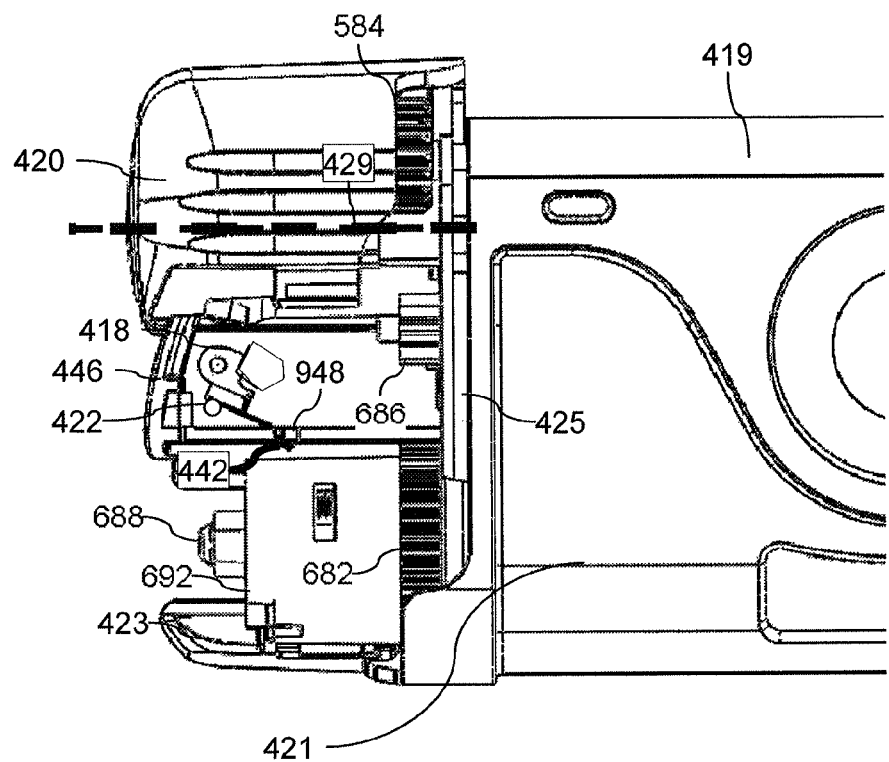
FIG. 9 is an overhead view of an exemplary embodiment of a drug delivery apparatus in a fully open state with cartridge fully inserted and doorstop in the non-obstructing mode.
Figure 15A:
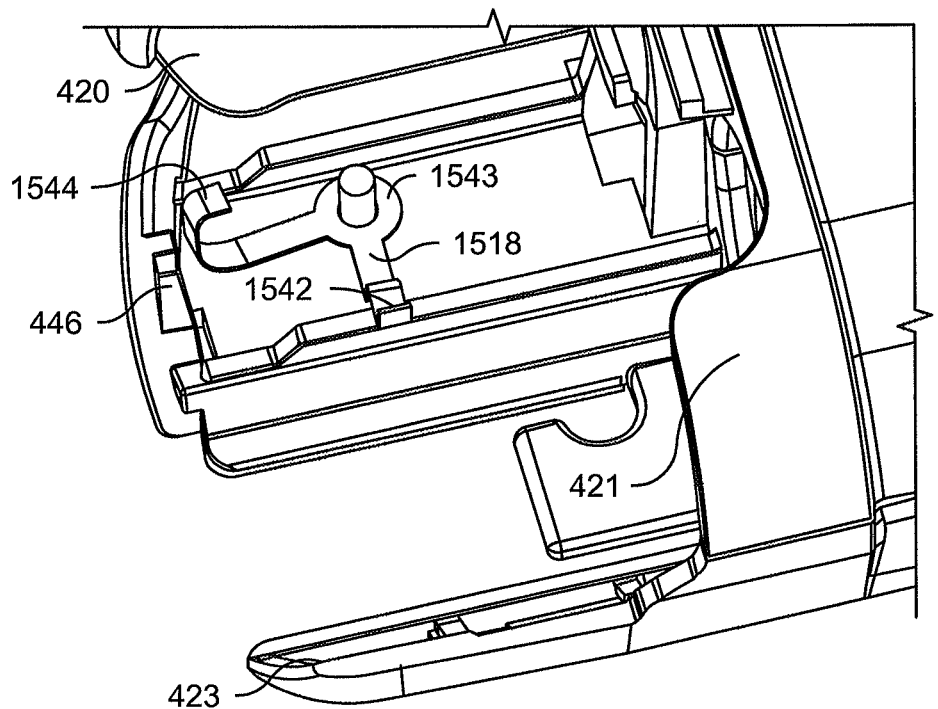
FIG. 15A is a detail perspective view of an alternative exemplary embodiment of a drug delivery apparatus in an open state showing a doorstop in a obstructing mode.
Figure 15B:
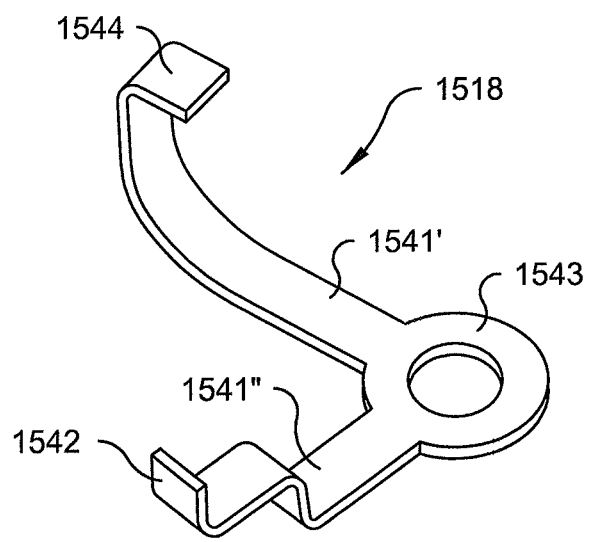
FIG. 15B is a detail perspective view of an alternative exemplary embodiment of a doorstop.

Referring now to the figures, FIG. 9 illustrates an overhead view of a drug delivery apparatus in an open state with doorstop 418 is a non-obstructing mode. Optionally, inserting cartridge 624 rotates doorstop 418 into the non-obstructing mode until it collides with a pin 948. Optionally in the non-obstructing mode, spacer 442 extends into the path of cartridge 624. For example, if a user were to try to remove cartridge 624, flange 626 will contact the extended spacer 442 and push doorstop 418 back into the obstructing mode, impeding removal of the cartridge and preventing closing of door 420. For example, incorrectly trying to remove the cartridge after piercing the septum may disable the apparatus and cause the user to return to the hospital for proper treatment. Alternatively or additionally, (for example as illustrated in FIGS. 15A-C) in the non-obstructing mode, doorstop may impede removal of the cartridge without returning to the obstructing mode. For example, the user would be impeded from removing the cartridge, but would be able to continue with the drug delivery.

Referring now to the figures, FIG. 10 illustrates a side view of an exemplary embodiment of a drug delivery apparatus in a closed state. In the closed state door 420 may optionally be flush to and/or not protrude from housing 419. Optionally, door 420 may permanently lock upon moving to the closed state. Alternatively or additionally, door 420 may be temporarily latched in the closed state and/or permanently locked at a later time.

An Exemplary Transmission Mechanism for an Exemplary Embodiment of a Drug Delivery Apparatus Referring now to the figures, FIGS. 11A-D illustrate various views of an exemplary transmission mechanism for a drug delivery apparatus. In the exemplary embodiment, a coupler 584 mounted on door 420 transmits power from a motive element 686 of the apparatus to a movable element 682 of cartridge 624.

Referring now to the figures, FIG. 11A is a side view of exemplary apparatus with door 420 in the open state. In the exemplary embodiment coupler 584 includes a gear. In the exemplary apparatus, movable element 682 includes a gear. It can be seen that, with door 420 is the open state coupler 584 is optionally disengaged from movable element 682.

Referring now to the figures, FIG. 11B is a rear view of exemplary apparatus with door 420 in the open state. In the exemplary apparatus, motive element 686 includes a gear. When door 420 is in the open state, motive element 686 and movable element 682 are optionally disengaged. In FIG. 11B a latch 1123 can be seen. Optionally latch 1123 latches door 420 to rear support 446 when door 420 is in a closed state.

Referring now to the figures, FIG. 11C illustrates a side cutaway view of exemplary drug delivery apparatus in a closed state. FIG. 11C illustrates an optional hub 599. In some embodiments, hub 599 may be mounted on an inside surface of door 420. When door 420 is in a closed state, hub 599 may optionally support projection 688. Projection 688 may optionally protrude from cartridge 624. For example, projection 688 may protrude from a rear end of telescoping assembly 692. When door 420 is in a closed state, hub 599 may optionally act as a counter force when telescoping assembly expands, for example forcing a plunger 693 into cartridge 624. Optionally, forcing plunger 693 into cartridge 624 may cause delivery of a drug.

In some embodiments, when door 420 is in a closed state a supporting structure may engage and/or support door 420. For example, in FIG. 11C a lip 1126 on door 420 is shown engaged to a groove 425 on apparatus housing 419. When engaged to lip 1126, groove 425 may support door 420.

Figure 11D:
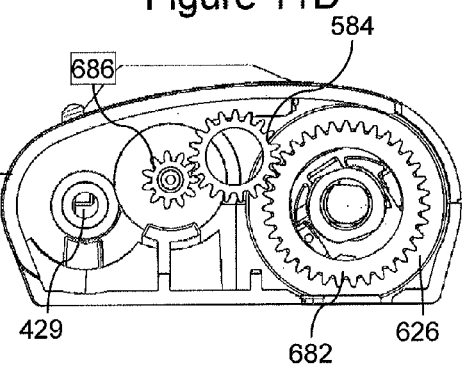
FIG. 11D is a detail rear cutaway view of an exemplary embodiment of a drug delivery apparatus in an closed state showing a coupler coupling a movable element of a cartridge to a motive element of the drug delivery apparatus.

Referring now to the figures, FIG. 11D illustrates a rear cutaway view of an exemplary apparatus with door 420 in the closed and/or permanently locked state. Optionally when door 420 is in the closed and/or locked state coupler 584 engages motive element 686 to movable element 682. Optionally, movable element 682 may transmit power to telescoping assembly 692. Optionally, power transmitted from motive element 686 through coupler 584 to movable element 682 may cause telescoping assembly 692 to expand, pushing plunger 693 into cartridge 624 delivering the drug.

Alternative Embodiments of a Doorstop for a Drug Delivery Apparatus

Referring now to the figures, FIGS. 12A-D illustrate various views of an exemplary alternative embodiment of a door locking mechanism for a drug delivery apparatus. In the exemplary embodiment of FIGS. 12A-D, a fixed end of a pin 1296 is mounted on a door 1220. Optionally, when there is no cartridge 624 in the apparatus, pin 1296 does not affect movement of door 1220. For example, without cartridge 624, door 1220 may open and close freely.

Figure 12A:
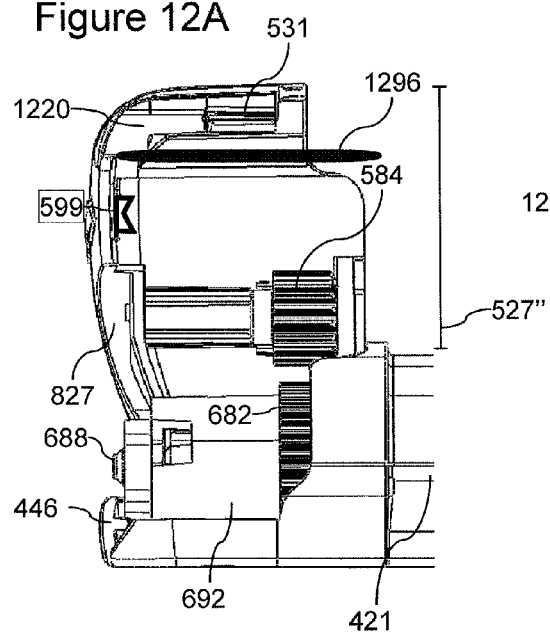
FIG. 12A is a detail side view of an alternative exemplary embodiment of a drug delivery apparatus in an open state showing a doorstop in an unlocked mode.

Referring now to the figures, FIG. 12A is a side view illustrating an exemplary embodiment of door 1220 in the open state.

Figure 12B:
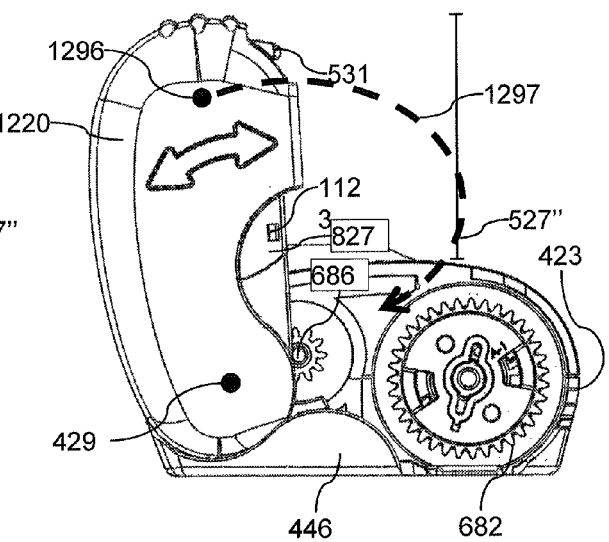
FIG. 12B is a detail rear view of an alternative exemplary embodiment of a drug delivery apparatus in an open state showing movement of a doorstop from an unlocked to a locked mode.

Referring now to the figures, FIG. 12B is a rear view illustrating and exemplary embodiment of door 1220 in the open state. Optionally, when cartridge 624 is inserted into the apparatus and door 1220 is closed, cartridge 624 diverts the free end of pin 1296 under groove 425 and the associated supporting structure (for example as illustrated in by the dark dashed line 1297 of FIG. 12B)

Figure 12C:
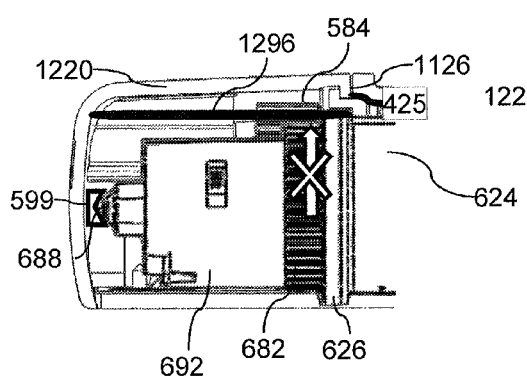
FIG. 12C is a detail side cutaway view of an alternative exemplary embodiment of a drug delivery apparatus in a closed state showing a doorstop in a locked mode.
Figure 12D:
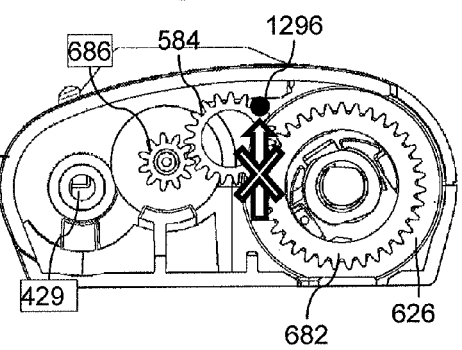
FIG. 12D is a detail rear cutaway view of an exemplary alternative embodiment of a drug delivery apparatus in a closed state showing a doorstop in a locked mode.

Referring now to the figures, FIG. 12C illustrates a side cutaway view of an exemplary drug delivery apparatus with door 1220 in a closed state. FIG. 11D illustrates a rear cutaway view of an exemplary apparatus with door 1220 in the closed and/or permanently locked state. Optionally when door 1220 is in the closed and/or locked state with cartridge 624 inserted, the free end of pin 1296 is trapped under groove 425 and the associated supporting structure permanently and/or temporarily locking and/or latching door 1220 in a closed state.

Figure 13A:
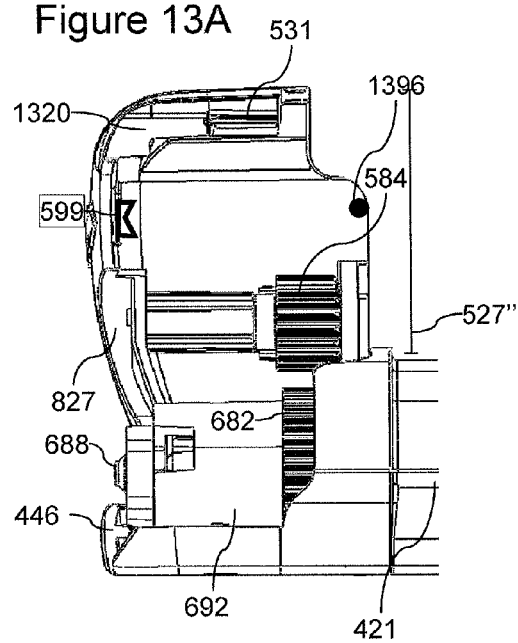
FIG. 13A is a detail side view of an alternative exemplary embodiment of a drug delivery apparatus in an open state showing a doorstop in a obstructing mode.
Figure 13C:
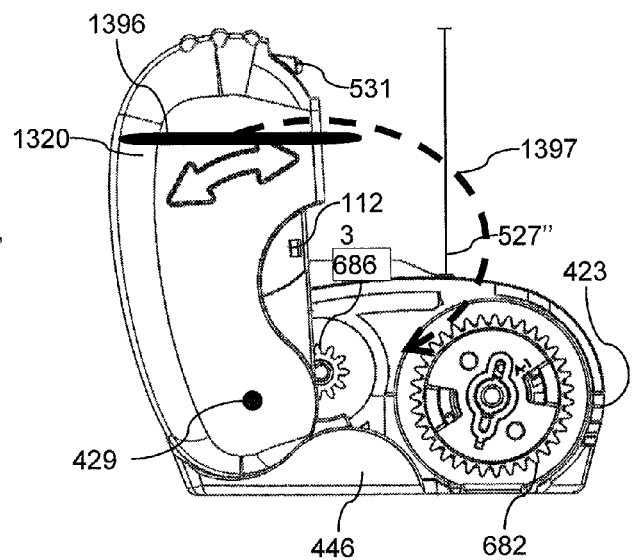
FIG. 13C is a detail rear view of an alternative exemplary embodiment of a drug delivery apparatus in an open state showing movement of a doorstop from a obstructing to a non-obstructing mode.
Figure 13B:
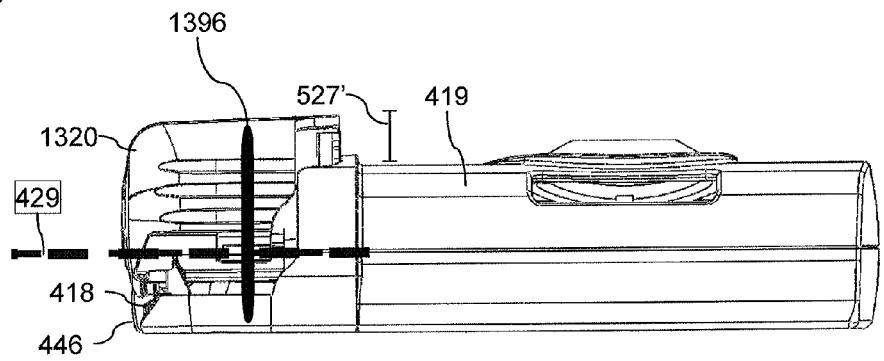
FIG. 13B is a detail side cutaway view of an alternative exemplary embodiment of a drug delivery apparatus in a transport state showing a doorstop in a obstructing mode, preventing closing of a door.

Referring now to the figures, FIGS. 13A-C illustrate various views of an exemplary alternative embodiment of a doorstop for a drug delivery apparatus. In the exemplary embodiment of FIGS. 13A-C, a fixed end of a pin 1396 is mounted on a door 1320.

Referring now to the figures, FIG. 13A is a side view illustrating an exemplary embodiment of door 1320 in the open state.

Referring now to the figures, FIG. 13B illustrates a side cutaway view of an exemplary drug delivery apparatus with door 1320 in a transport state. Optionally, when an attempt is made to close door 1320 when there is no cartridge 624 in the apparatus, pin 1396 props up door 1320, preventing door 1320 from closing (for example as illustrated in FIG. 3C).

Referring now to the figures, FIG. 13C is a rear view illustrating and exemplary embodiment of door 1320 in the open state. Optionally, when cartridge 624 is inserted into apparatus housing 419 and door 1320 is closed, cartridge 624 diverts the free end of pin 1396 sideways (as illustrated for example by dark dashed lines 1397 in FIG. 13C). Diverting the free end of pin 1396 may optionally prevent pin 1396 from propping up door 1320, allowing door 1320 to close and/or lock.

Figure 14A:
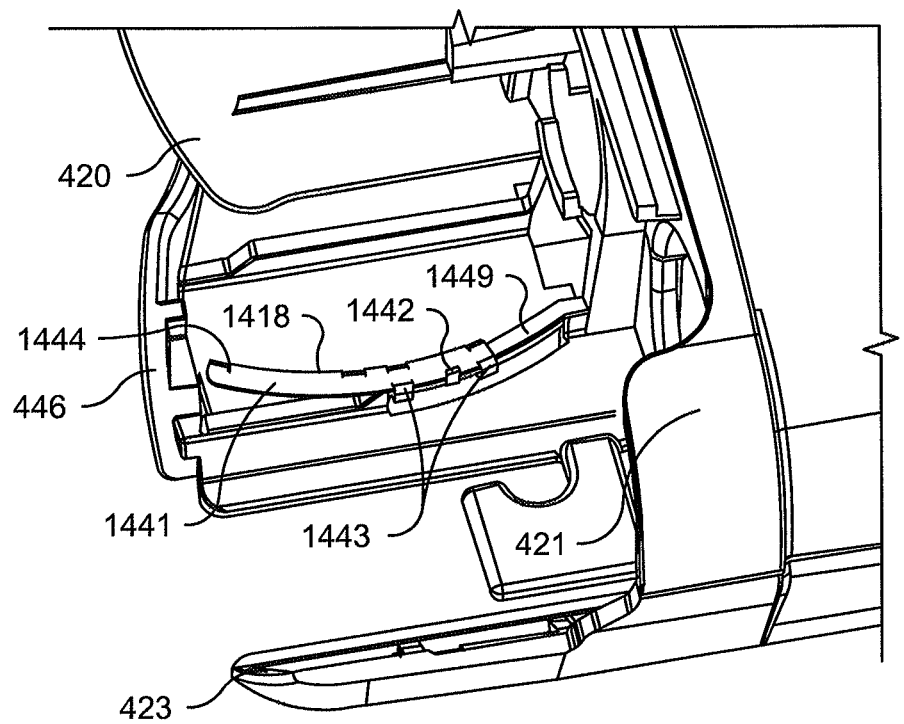
FIG. 14A is a detail perspective view of an alternative exemplary embodiment of a drug delivery apparatus in an open state showing a doorstop in a obstructing mode.
Figure 14B:
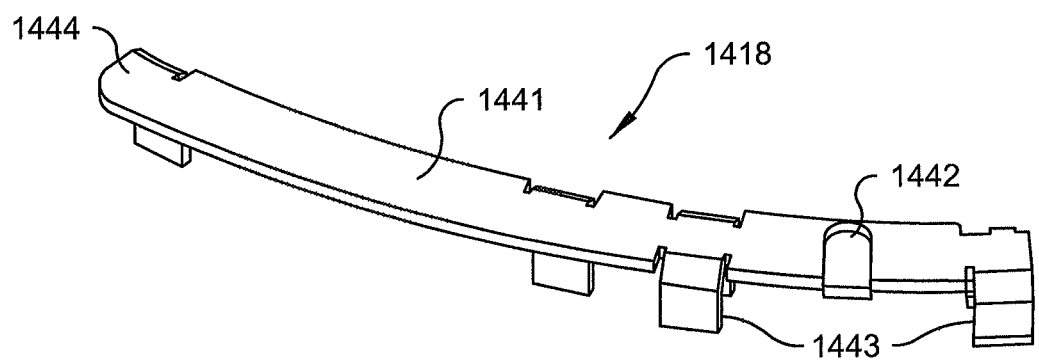
FIG. 14B is a detail perspective view of an alternative exemplary embodiment of a doorstop.

Referring now to the figures, FIGS. 14A-B illustrate various views of an exemplary alternative embodiment of a doorstop for a drug delivery apparatus. FIG. 14A illustrates a perspective view of an exemplary embodiment of a sliding doorstop 1418 in an obstructing mode. In the obstructing mode, a door obstructing flange 1444 may optionally obstruct closing of door 420. As a cartridge is inserted into a canal 421, the cartridge may optionally collide with a cartridge contacting spacer 1442. Further inserting the cartridge may optionally slide doorstop 1418 forward along a track 1449 into a non-obstructing mode. In the non-obstructing mode, flange 1444 may be moved out of the way of door 420 allowing closing of door 420. FIG. 14B illustrates a detailed perspective view of exemplary doorstop 1418. Doorstop 1418 optionally includes sliding mounts 1443. Doorstop 1418 optionally includes a curved extension 1441. In the obstructing mode, extension 1441 optionally holds flange 1444 in path of door 420. Spacer 1442 optionally projects into the path of cartridge 624 entering channel 421.

Referring now to the figures, FIGS. 15A-B illustrate various views of an exemplary alternative embodiment of a doorstop for a drug delivery apparatus. FIG. 15A illustrates a perspective view of an exemplary embodiment of a rotating doorstop 1518 in an obstructing mode. In the obstructing mode, a door obstructing flange 1544 may optionally obstruct closing of door 420. As a cartridge (for example cartridge 624) is inserted into a channel 421, a flange on the rear of the cartridge (for example flange 626) may optionally collide with a cartridge contacting a spacer 1542. Further inserting the cartridge may optionally rotate doorstop 1518 about 90 degrees counter clockwise into a non-obstructing mode. In the non-obstructing mode, flange 1544 is moved out of the way of door 420 allowing closing of door 420. Doorstop 1518 optionally includes a rotating base 1543. Doorstop 1518 optionally includes two arms 1541' and 1541". In the obstructing mode, arm 1541' holds flange 1544 in path of door 420. In the obstructing mode, arm 1541" projects spacer 1542 into the path of cartridge 624 entering channel 421. In the non-obstruction mode arm 1541' holds flange 1544 in the exit path of the cartridge. Each arm 1541' and 1541" may optionally bend upward holding flange 1544 and spacer 1542 above base 1543. Arms 1541' and 1541" may optionally may extend at different angles from base 1543. For example, arms 1541' and 1541" may optionally may extend at right angles from each other.

In some embodiments, a user will be prevented from removing a cartridge when doorstop 1518 is in the non-obstructing mode. An attempt to remove the cartridge may optionally be blocked without disabling the drug delivery apparatus. For example, an attempt to remove a cartridge (for example cartridge 624) when doorstop 1518 is in the non-obstructing mode will optionally cause the cartridge flange (for example flange 626) to collide with flange 1544. After collision with flange 1544, further attempts remove the cartridge will optionally rotate doorstop 1518 about 45 degrees clockwise until spacer 1542 contacts the body of the cartridge. Optionally at the point where spacer 1542 contacts the body of the cartridge, doorstop 1518 may be prevented from further clockwise rotation. Optionally at the point where spacer 1542 contacts the body of the cartridge, flange 1544 may still be blocking the rear of the cartridge. Optionally at the point where spacer 1542 contacts the body of the cartridge, flange 1544 may not obstruct closing of door 420. Optionally at the point where spacer 1542 contacts the body of the cartridge, door 420 may be closed and the apparatus activated, but removal of the cartridge will optionally be prevented. FIG. 15B illustrates a detailed perspective view of exemplary doorstop 1518.

Figure 19A:
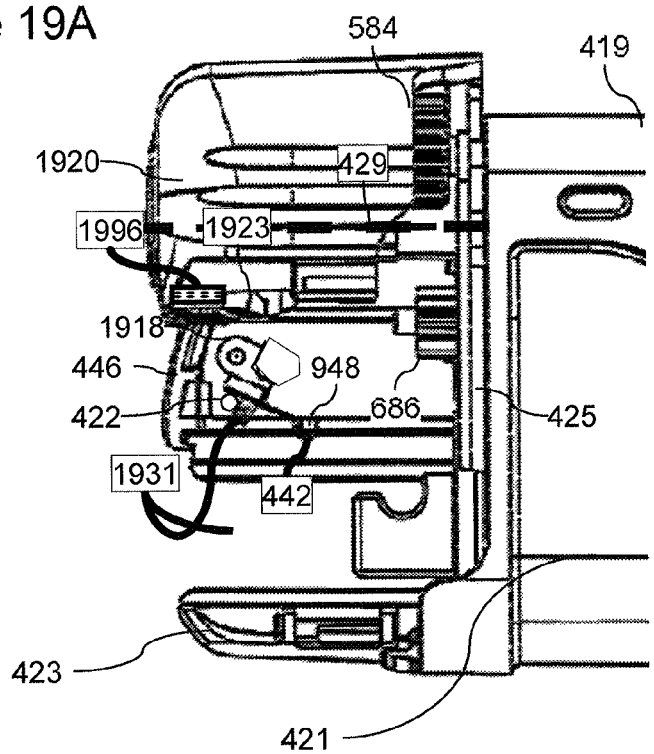
FIG. 19A is a detail overhead view of an alternative exemplary embodiment of a doorstop wherein the door is latched to the doorstop in a non-obstructing mode.
Figure 19B:
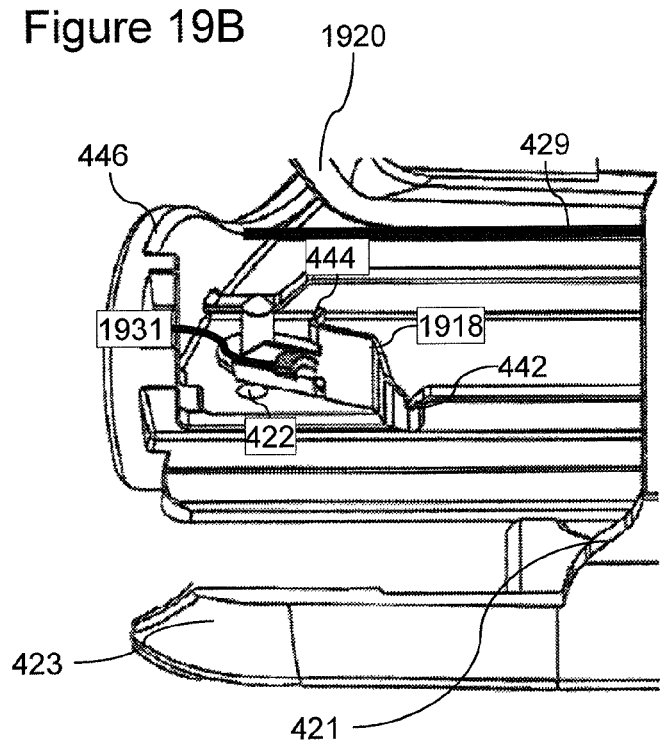
FIG. 19B is a detail perspective view of an alternative exemplary embodiment of a doorstop wherein the door is latched to the doorstop.

Referring now to the figures, FIGS. 19A-B illustrate various views of an exemplary alternative embodiment of a doorstop, wherein the door is latched to the doorstop. FIG. 19A illustrates an overhead view of an exemplary embodiment of a doorstop 1918 in a non-obstructing mode. Doorstop 1918 includes a hook 1931. Optionally, hook 1931 may optionally lock door 1920. In the example, a latch 1923 is provided. Optionally, latch 1923 is connected to the back end of door 1920 by a plate 1996. For example, hook 1931 is positioned such that when doorstop 1918 is in the non-obstructing mode and door 1920 is closed, latch 1923 catches hook 1931 locking door 1920. Optionally hook 1931 is positioned such that when doorstop 1918 is in the obstructing mode, if a user closes door 1920 (for example by using force to deform door 1920) latch 1923 will not catch hook 1931 and door 1920 will not lock. Optionally, when latch 1923 is caught on hook 1931 door 1920 is permanently locked. FIG. 19B illustrates a detailed perspective view of exemplary doorstop 1918 and hook 1931.

Various embodiments and aspects of the present invention as delineated hereinabove and as claimed in the claims section below find support in the following examples.

EXAMPLES

Reference is now made to the following examples, which together with the above descriptions illustrate some embodiments of the invention in a non limiting fashion.

Force Graphs

Figure 16A:
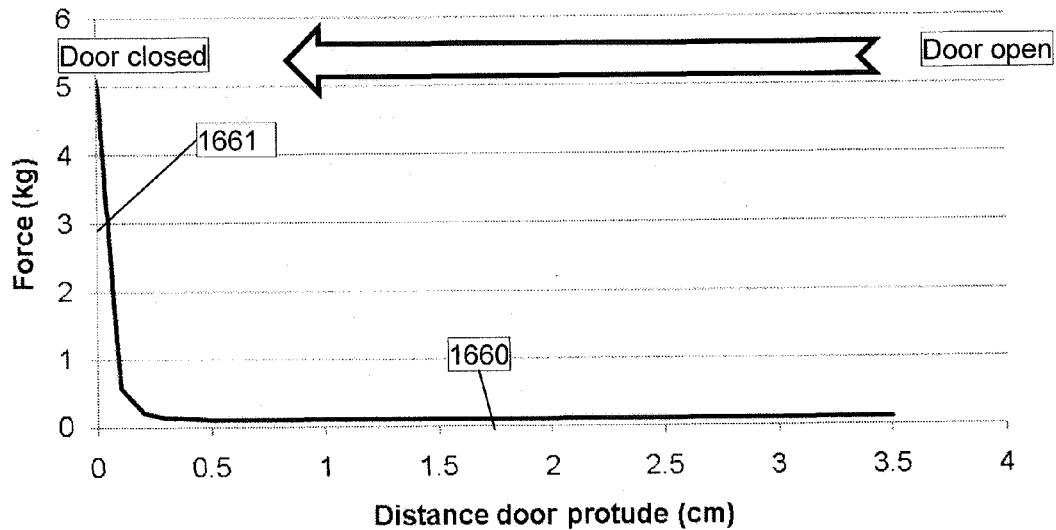
FIG. 16A is a schematic chart of force needed to close a drug delivery apparatus door versus the distance door protrudes from a housing of the drug delivery apparatus for the doorstop in the obstructing mode.

Referring now to the Figures, FIG. 16A shows an exemplary simulated graph of force to close a door vs. distance a door is protruding for a drug delivery apparatus housing (for example housing 419) with the doorstop in an obstructing mode. The flat low portion 1660 of the graph for protrusion between 3.5 cm and 0.3 cm indicates that the door moves easily between the fully open state (door protruding 4.3 cm) and the transport state (door protruding about 0.3 cm). The sharp peak 1661 for closing the door past 0.3 cm indicates that the doorstop is obstructing moving from the transport state to the closed state (door not protruding). In the example, the force entailed in closing the door with the doorstep in the obstructing mode is (peak 1661) approximately 5 kg, optionally, the force entailed may differ. In some embodiments, the force may be greater. In the exemplary embodiment, the maximum protrusion of the door is about 3.5 cm. In some embodiments the maximum protrusion of the door may range for example between 2 and 5 cm. In the exemplary embodiment, the doorstop obstructs the door for protrusions less than 0.3 cm. In some embodiments, the door stop may obstruct the door for example starting at protrusions ranging for example between 0.05 to 0.5 cm and/or less. Alternatively or additionally, a doorstop may allow a door to close, but prevent it from latching.

Figure 16B:
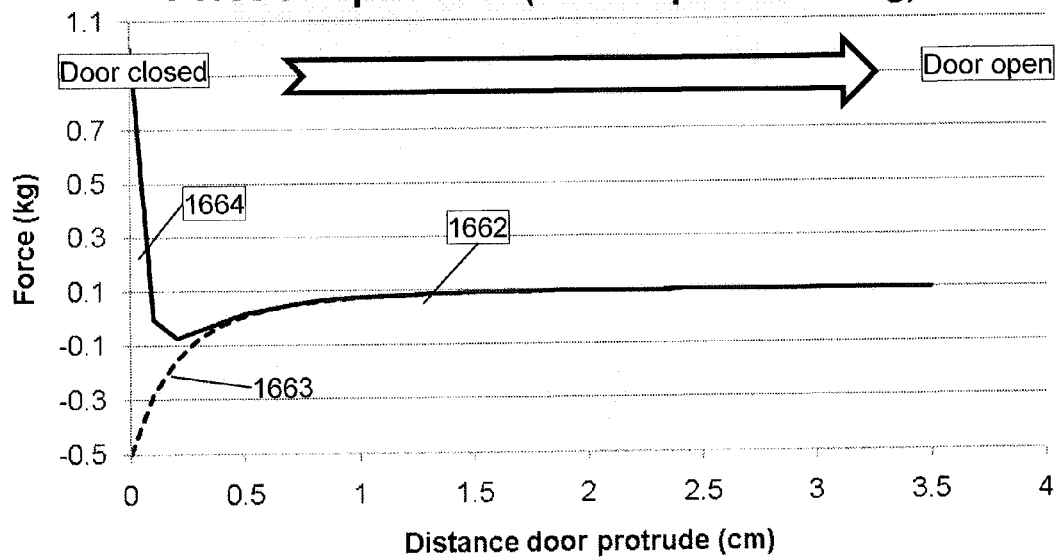
FIG. 16B is a schematic chart of force needed to open a drug delivery apparatus door versus the distance door protrudes from a housing of the drug delivery apparatus for the doorstop in the obstructing mode.

Referring now to the Figures, FIG. 16B shows an exemplary simulated graph of force to open a door vs. distance a door is protruding for a drug delivery apparatus housing (for example housing 419) with the doorstop in an obstructing mode. The flat low portion 1662 of the graph for protrusion between 3.5 cm and 0.3 cm indicates that the door moves easily between the fully open state (door protruding 3.5 cm) and the transport state (door protruding about 0.3 cm). Optionally it may be difficult to close the door when the doorstep is in the obstructing position. In some cases, a user may force the door closed. For an embodiment without an optional temporary latch, the force 1663 decreases below zero for protrusions less than 0.3 cm. With the doorstop in the obstructing mode and for example without an optional temporary latch, the door may optionally spontaneously open from the closed mode to the transport mode. The force spontaneously opening the door in the exemplary embodiment is shown as for example −0.5 kg. Optionally the force may be different. In some embodiments the magnitude of the force may be greater than 0.5 kg. Alternatively or additionally, in an embodiment with an optional temporary latch, the door may latch closed even when the doorstop is in an obstructing mode. Then as small force 1664 would optionally be entailed to reopen the door. In the exemplary embodiment the force entailed in opening the latch is approximately 0.9 kg. Optionally the force to open a temporary latch may range for example between 0.3 and 4.5 kg or more.

Figure 17A:
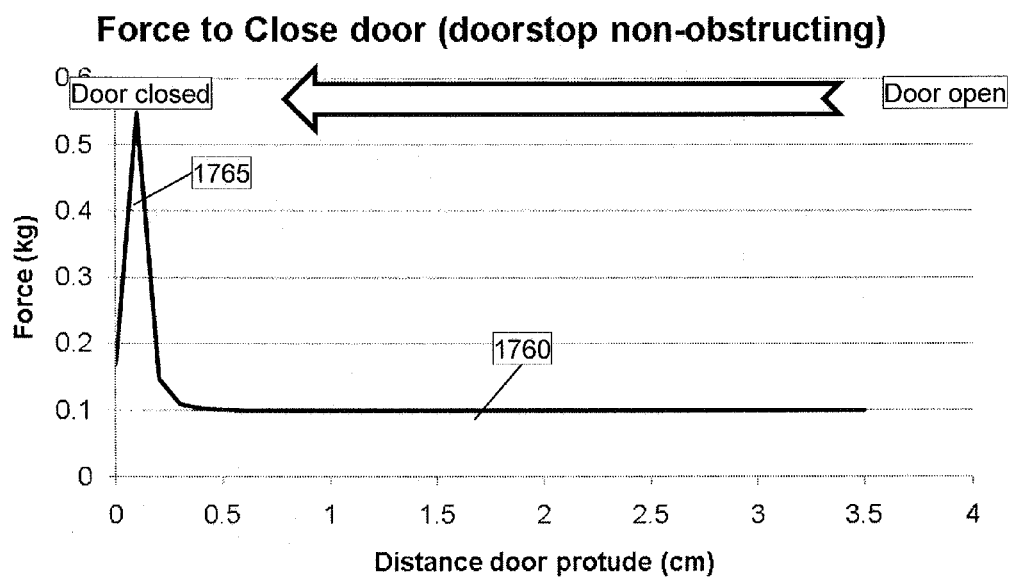
FIG. 17A is a schematic chart of force needed to close a drug delivery apparatus door versus the distance the door protrudes from a housing of the drug delivery apparatus of the apparatus for the doorstop in the non-obstructing mode.

Referring now to the Figures, FIG. 17A shows an exemplary simulated graph of force to close a door vs. distance a door is protruding for a drug delivery apparatus housing (for example housing 419) with the doorstop in a non-obstructing mode. The flat low portion 1760 of the graph for protrusion between 3.5 cm and 0.3 cm indicates that the door moves easily between the fully open state (door protruding 3.5 cm) and the transport state (door protruding about 0.3 cm). The shallow peak 1765 for closing the door past 0.1 cm indicates that a small force causes latching and/or locking of the door. In some embodiments closing the latch could require for example between 0.1 and 4.5 kg.

Figure 17B:
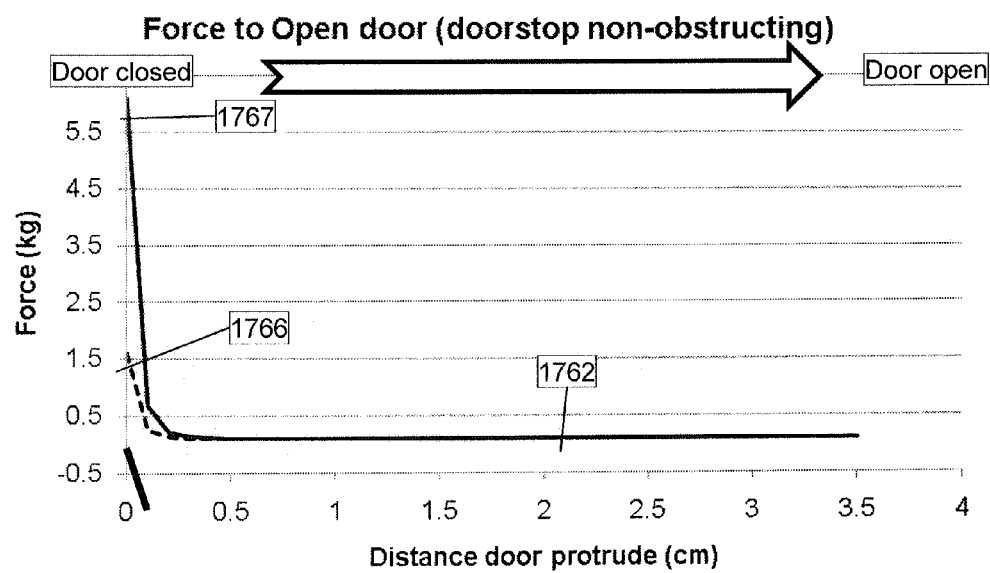
FIG. 17B is a schematic chart of force needed to open a drug delivery apparatus door versus the distance door protrudes from a housing of the drug delivery apparatus for the doorstop in the non-obstructing mode.

Referring now to the Figures, FIG. 17B shows an exemplary simulated graph of force to open a door vs. distance a door is protruding for a drug delivery apparatus housing (for example housing 419) with the doorstop in a non-obstructing mode. The flat low portion 1762 of the graph for protrusion between 3.5 cm and 0.3 cm indicates that the door moves easily between the fully open state (door protruding 3.5 cm) and the transport state (door protruding about 0.3 cm). For an embodiment that is optionally closed with a temporary latch, a small force 1766 is entailed to unlatch the door to move from the closed mode to the transport and/or open mode. In the exemplary embodiment, the force entailed in unlatching the temporary latch is approximately 1.5 kg. In some embodiments, the force to open a temporary latch may range, for example between 0.3 and 5 kg. Alternatively, when the door is locked, a very significant force 1767 would optionally be entailed to reopen the door (for example by breaking the lock and/or the door and/or the apparatus). In the exemplary embodiment, the force entailed opening the lock is approximately 6 kg. In some embodiments, the force to open a lock may range, for example from 5 kg to 20 and/or 50 kg and/or more.

Figure 18A:
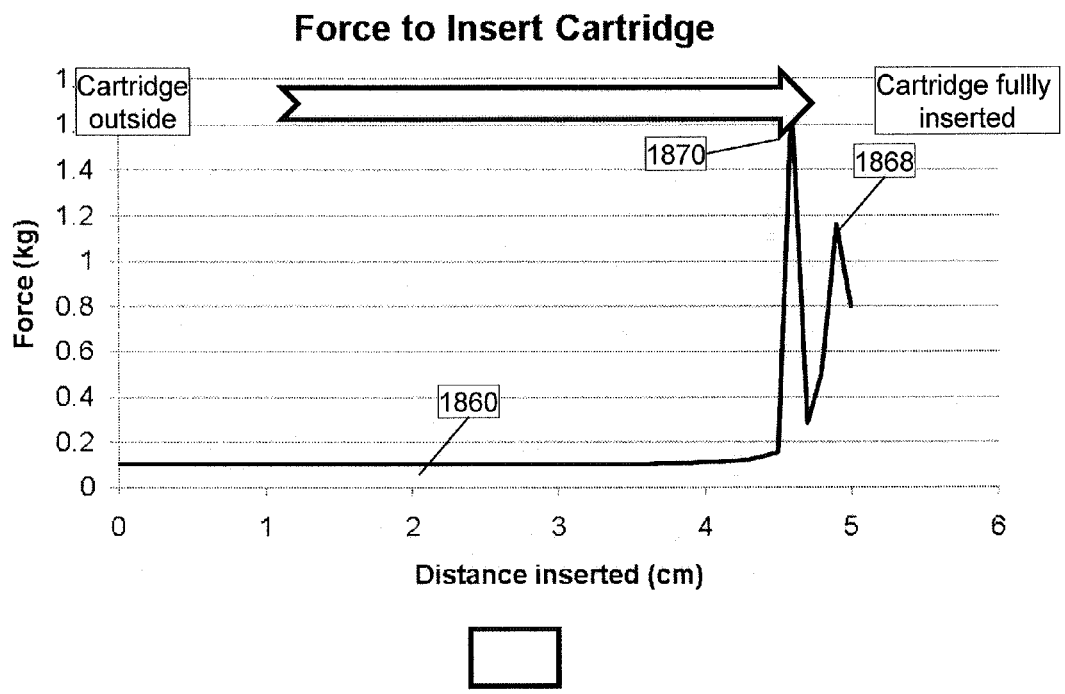
FIG. 18A is a schematic chart of force needed to insert a cartridge into a drug delivery apparatus for the doorstop in the obstructing mode.

Referring now to the Figures, FIG. 18A shows an exemplary simulated graph of force to insert a cartridge vs. distance inserted for a drug delivery apparatus with the doorstop starting in an obstructing mode. The flat low portion 1860 of the graph for insertion between 0 cm and 4.8 cm indicates that the cartridge moves freely until it is almost entirely inserted. The shallow peak 1870 for inserting the cartridge past 4.6 cm indicates that a small force may optionally be entailed to move the doorstop from the obstructing mode to the non-obstructing mode. For example the force may be entailed to push the doorstop over a stabilizer (for example stabilizer 422). Alternatively or additionally, a stabilizer may not be including. Optionally, peak 1870 may range for example between 0 and 1.5 kg. Alternatively or addition, the point at which the cartridge engages the doorstop may range between 0.1 cm and 10 cm of insertion. Optionally, after the cartridge passes the doorstop, it may be primed, for example by puncturing a septum. Puncturing a septum may optionally entail an extra force 1868 at the for example in the last 1-5 millimeter or so of insertion. Alternatively or additionally, there may be an optional latch locking the cartridge into the canal and there may be an extra force required to pass that latch.

Figure 18B:
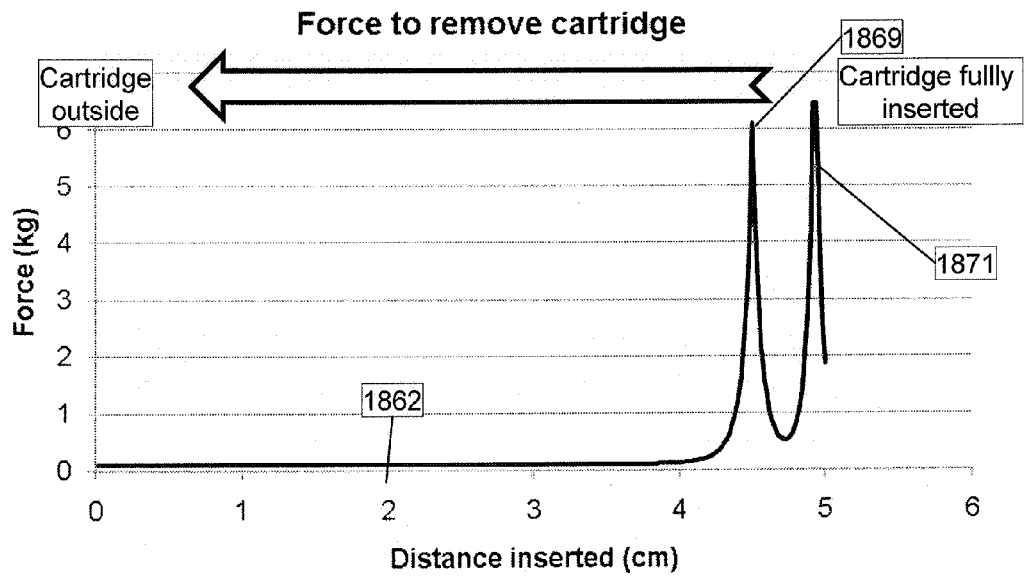
FIG. 18B is a schematic chart of force needed to remove a cartridge into a drug delivery apparatus for the doorstop in the non-obstructing mode.

Referring now to the Figures, FIG. 18B shows an exemplary simulated graph of force to remove a cartridge vs. the insertion depth of the cartridge tip in a drug delivery apparatus with the doorstop in a non-obstructing mode, for an embodiment wherein the doorstop optionally impedes removal of the cartridge. The first movements for a fully inserted cartridge may entail a force 1871, for example to pull a needle out of the septum and/or to pass an optional locking latch locking the cartridge in the fully inserted position. Optionally, a force 1869 is entailed to move the cartridge past the doorstop (for example by breaking the doorstop and/or the cartridge and/or the apparatus). Alternatively, the doorstop may optionally not impede removal of the cartridge in which case the peak in force 1869 may not occur. The flat low portion 1862 of the graph for removing the cartridge after the flange has cleared the doorstop (at about 0.3 cm) indicates that once the cartridge has cleared the doorstop and when the door is open, the cartridge may optionally be removed easily. The force of peaks 1869 and 1871 are shown as about 6 kg. Alternatively the force to for the cartridge to pass a locking latch or the doorstop may range for example between 1 and 20 kg or more. Alternatively or additionally, the doorstop may not block removal of the cartridge and/or there may not be a locking latch blocking removal of the cartridge).

Caveats

As used herein the term "about" refers to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An insertion assembly for a cartridge in a drug delivery apparatus comprising:

an apparatus housing; a channel for insertion of the cartridge formed in said housing;

a door to an opening of said channel, the door being pivotable relative to the channel to open or close the channel; and a doorstop including a flange, and an extension, wherein said doorstop has two modes, an obstructing mode wherein said flange obstructs closing of said door and wherein said extension extends to a path of insertion of the cartridge into said channel, and a non-obstructing mode wherein said door may close unobstructed by said doorstop, wherein, when the cartridge is inserted into said channel, the cartridge engages said extension moving said doorstop to said non-obstructing mode, and wherein in said non-obstructing mode said doorstop blocks an exit of said channel, impeding removal of the cartridge from said channel.

2. The assembly of claim 1, wherein further including a base, and wherein said flange is held above said base in said obstructing mode, such that when said door rests on said flange said door protrudes from said housing by a predetermined distance.

3. The assembly of claim 1 wherein said doorstop includes a rotating base and wherein said doorstop rotates from said obstructing mode to said non-obstructing mode.

4. The assembly of claim 1, wherein said doorstop includes a sliding base and wherein said doorstop slides from said obstructing mode to said non-obstructing mode.

5. The assembly of claim 1, wherein the cartridge includes a flange and said engaging is by said cartridge flange.

6. The assembly of claim 1 wherein said door has at least three states:

a fully open state wherein said door clears an opening to said channel enough to allow insertion of a cartridge into said channel and wherein in said fully open state said door protrudes from said apparatus, a transport state wherein said door at least partially obstructs said opening and wherein in said transport state said door protrudes from said apparatus less than said protruding during said open state, and a fully closed state wherein said door obstructs said opening enough to prevent both insertion and removal of the cartridge through said opening;

and wherein said door moves freely between said transport state and said fully open state.

7. The assembly of claim 6, wherein said door comprises a notch on an inside surface thereof, said notch supporting a projection from the cartridge when said door is in said closed state.

8. The assembly of claim 6, wherein said door is mounted on a pivot and wherein said door pivots between said states.

9. The assembly of claim 1 wherein said door includes a coupler, said coupler located such that in when said door is in said closed state said coupler couples a movable element of the cartridge to a motive element in apparatus.

10. The assembly of claim 1, further comprising:

a latch and wherein, in said fully closed state said latch reversibly latches said door.

11. The assembly of claim 1, further comprising:

a latch and wherein, in said closed state said latch permanently locks said door.

12. The assembly of claim 11, wherein in said permanently locked state said door is latched to said doorstop in said non-obstructing mode.

13. The assembly of claim 12, further comprising:

a hook mounted to said doorstop and wherein latching is to said hook.

14. The assembly of claim 1, further comprising:

a stabilizer maintaining said doorstop in said obstructing mode, until a force greater than a threshold value moves said doorstop into said non-obstructing mode.

15. The assembly of claim 1, wherein the door is pivotable about a first axis parallel to a plane of the opening of the cartridge channel and wherein the doorstop is rotatable about a second axis which is perpendicular to the first axis.

* * * * *